United States Patent
Kim

(10) Patent No.: US 11,685,890 B2
(45) Date of Patent: Jun. 27, 2023

(54) FERMENTATION AND AGING APPARATUS AND METHOD FOR CONTROLLING FERMENTATION AND AGING APPARATUS

(71) Applicant: LG ELECTRONICS INC., Seoul (KR)

(72) Inventor: Sungjoo Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 12 days.

(21) Appl. No.: 15/930,588

(22) Filed: May 13, 2020

(65) Prior Publication Data

US 2020/0362291 A1 Nov. 19, 2020

(30) Foreign Application Priority Data

May 14, 2019 (KR) .................. 10-2019-0056431

(51) Int. Cl.
*C12M 1/34* (2006.01)
*C12M 1/00* (2006.01)
(Continued)

(52) U.S. Cl.
CPC ............ *C12M 41/12* (2013.01); *C12M 29/00* (2013.01); *C12M 41/48* (2013.01); *C12M 47/00* (2013.01);
(Continued)

(58) Field of Classification Search
CPC .... F24H 9/2007; F24H 15/175; F24H 15/305; C12M 41/16; C12M 41/24; C12M 41/12
See application file for complete search history.

(56) References Cited

U.S. PATENT DOCUMENTS 4,682,728 A * 7/1987 Oudenhoven ...... G05D 23/1393
700/285
5,352,095 A 10/1994 Tanaka et al.
(Continued)

FOREIGN PATENT DOCUMENTS

| EP | 0 573 734 | 12/1993 |
| EP | 3 246 389 | 11/2017 |
| KR | 10-2017-0130257 | 11/2017 |

OTHER PUBLICATIONS

European Search Report issued in Application No. 20174363.0 dated Oct. 12, 2020.
Korean Office Action dated Dec. 21, 2020.

*Primary Examiner* — Jonathan M Hurst
(74) *Attorney, Agent, or Firm* — Ked & Associates, LLP

(57) ABSTRACT

A fermentation and aging apparatus and a method for controlling a fermentation and aging apparatus are provided. The fermentation and aging apparatus may include a tank in which a fluid, such as water may be accommodated, a fermentation container forming a space in which the fluid discharged from the tank may be accommodated, a pump disposed in a channel between the tank and the fermentation container to supply the fluid accommodated in the tank to the fermentation container, a flow rate control valve configured to control a flow rate of the fluid discharged from the tank, a heater configured to heat the fluid discharged from the tank, a temperature sensor configured to measure a temperature of the fluid passing through the heater, and a controller configured to control a degree of opening of the flow rate control valve based on the measured temperature.

11 Claims, 8 Drawing Sheets

(51) Int. Cl.
*C12M 1/36* (2006.01)
*C12C 11/07* (2006.01)
*C12C 13/10* (2006.01)
*C12H 1/22* (2006.01)

(52) U.S. Cl.
CPC .............. *C12C 11/07* (2013.01); *C12C 13/10* (2013.01); *C12H 1/22* (2013.01)

(56) References Cited

U.S. PATENT DOCUMENTS

2016/0007798 A1 1/2016 Jimenez
2017/0335256 A1* 11/2017 Park ...................... C12C 11/006
2019/0300827 A1* 10/2019 Liang .................... C12C 11/006

* cited by examiner

FERMENTATION AND AGING APPARATUS AND METHOD FOR CONTROLLING FERMENTATION AND AGING APPARATUS

CROSS-REFERENCE TO RELATED APPLICATION(S)

This application claims priority under 35 U.S.C. 119 and 365 to Korean Patent Application No. 10-2019-0056431, filed in Korea on May 14, 2019 in the Korean Intellectual Property Office, the disclosure of which is incorporated herein by reference.

BACKGROUND

1. Field

A fermentation and aging apparatus and a method for controlling fermentation and aging apparatus are disclosed herein.

2. Background

Beverages are collectively referred to as drinkable liquids, such as alcohol or tea. For example, beverages may be divided into various categories, such as water (a beverage) for quenching thirst, juice beverages with a unique flavor and taste, refreshing beverages giving a refreshing sensation, favorite beverages with a stimulant effect, or alcoholic beverages with an alcohol effect.

A representative example of such a beverage is beer. Beer is an alcoholic beverage produced by making juice of malt, which is made by sprouting barley, filtering the juice, adding hop, and fermenting yeast.

Consumers may purchase ready-made products made and sold by a beer maker or may make beer at home (hereinafter "homemade" beer) produced by directly fermenting beer ingredients at home or in a bar. Homemade beer may be made in a variety of types rather than ready-made products and may be made to better suit a consumer's taste.

The ingredients for making beer may include water, liquid malt, hop, yeast, and a flavoring additive, for example. Leaven, which is called yeast, may be added to liquid malt to ferment the liquid malt and assist production of alcohol and carbonic acid. Flavor additives are additives that enhance the taste of beer, such as fruit, syrup, and vanilla beans, for example.

Generally, homemade beer may include three stages or operations, namely, a wort stage or operation, a fermentation stage or operation, and an aging stage of operation, and it may take about two to three weeks from the wort stage or operation to the aging stage or operation. Maintaining an optimum temperature during the fermentation operation is important for homemade beer, and the easier the beer is to make, the more user convenience is improved.

Recently, a fermentation and aging apparatus capable of easily making a beer-like beverage at home or in a bar has been gradually used. Such a fermentation and aging apparatus is configured to be convenient.

BRIEF DESCRIPTION OF THE DRAWINGS

Embodiments will be described in detail with reference to the following drawings in which like reference numerals refer to like elements, and wherein.

DETAILED DESCRIPTION

Figure 1:
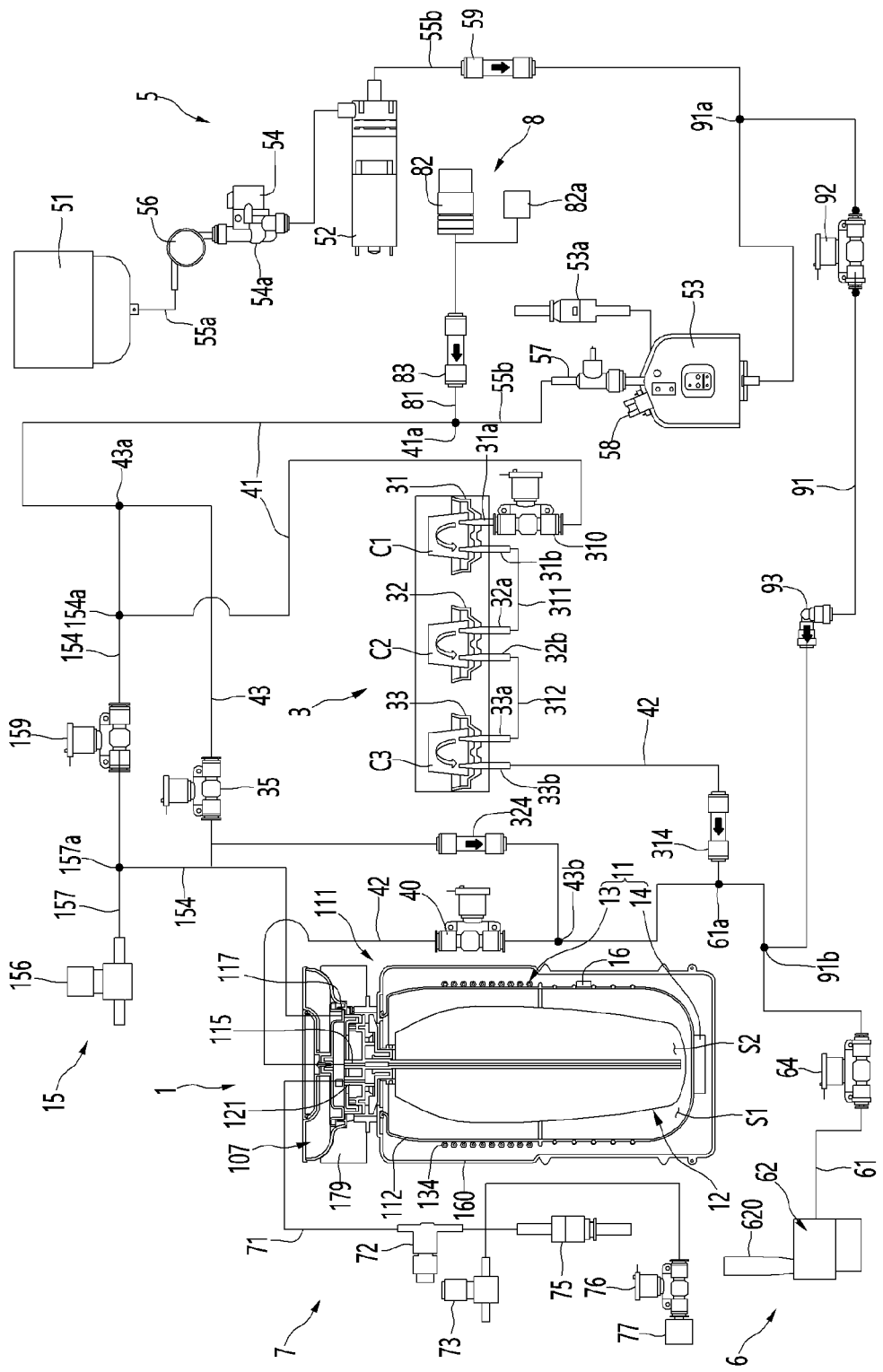
FIG. 1 is a schematic view of a fermentation and aging apparatus according to an embodiment.

Hereinafter, embodiments are described with reference to drawings. Wherever possible, like or the same reference numerals have been used to indicate like or the same elements, and repetitive disclosure has been omitted.

Although beer is exemplified as a beverage that is made using a fermentation and aging apparatus according to embodiments, the kind of beverage that can be made using the fermentation and aging apparatus is not limited to beer and various kinds of beverages may be made using the fermentation and aging apparatus according to embodiments.

FIG. 1 is a schematic view of a fermentation and aging apparatus according to an embodiment. The fermentation and aging apparatus may include a fermentation module 1. A beverage may be fermented in the fermentation module 1. The fermentation and aging apparatus may include a temperature controller that controls an inner temperature of the fermentation module 1.

The fermentation and aging apparatus may include a fluid supply module 5. The fluid supply module 5 may supply a fluid, such as water.

The fermentation and aging apparatus may include an ingredient supplier 3 provided with ingredient receivers 31, 32, and 33 in which ingredients required for making a beverage may be accommodated. The fermentation and aging apparatus may include main channels 41 and 42 that connect the fluid supply module 5 to the fermentation module 1.

The fermentation and aging apparatus may include a beverage dispenser 6 that dispenses the beverage made in the fermentation module 1 to the outside. The beverage dispenser 6 may be connected to second main channel 42. Thus, the beverage dispensed from the fermentation module 1 may be guided to the beverage dispenser 6 by passing through a portion of the second main channel 42.

The fermentation and aging apparatus may further include a gas discharger 7. The gas discharger 7 may be connected to the fermentation module 1 to discharge a gas generated while the beverage is made.

The fermentation and aging apparatus may further include an air injector 8 that injects air. The air injector 8 may be connected to the fluid supply module 5 or first main channel 41. The air injector 8 may include an air pump 82.

The fermentation and aging apparatus may further include an air controller 15 that controls a pressure between an inner wall of a fermentation tank 112 and an outer surface of a fermentation container 12. The fermentation and aging apparatus may further include a sub channel 91. The sub channel 91 may connect the fluid supply module 5 to the beverage dispenser 6.

The fermentation module 1 may include a fermentation tank module 111 having an opening, and a fermentation lid 107 that opens and closes the opening. The fermentation tank module 111 may include a fermentation case 160 and fermentation tank 112 accommodated in the fermentation case 160 and having an inner space S1. Insulation (not shown) may be provided between the fermentation case 160 and the fermentation tank 112. The fermentation tank module 111 may further include a lid seating body 179 on which the fermentation lid 107 may be seated.

Each of the fermentation case 160 and the fermentation tank 112 may be provided as an assembly of a plurality of members or components. The fermentation case 160 may define an outer appearance of the fermentation tank module 111.

The fermentation lid 107 may seal an inside of the fermentation tank module 111 and be disposed on the fermentation tank module 111 to cover the opening. A main channel, more particularly, a main channel connecting portion 115 connected to the second main channel 42 may be provided in the fermentation lid 107.

A fermentation container 12 may be accommodated in the fermentation tank 112. The fermentation container 12 may be provided as a separate container so that beverage ingredients and a finished beverage do not stain the inner wall of the fermentation tank 112. The fermentation container 12 may be separably disposed on or in the fermentation tank 112. The fermentation container 12 may be seated on or in the fermentation tank 112 to ferment the beverage within the fermentation tank 112. After the fermentation container 12 is used, the fermentation container 12 may be removed from the fermentation tank 112.

The fermentation container 12 may be a pack containing ingredients (ingredients to be fermented) for making a beverage. The fermentation container 12 may be made of a flexible material. Thus, the fermentation container 12 may be easily inserted into the fermentation tank 112 and be contracted and expanded by a pressure. However, embodiments are not limited thereto. For example, the fermentation container 12 may be made of a PET material.

The fermentation container 12 may have a beverage-making space S2 in which beverage ingredients may be accommodated, and the beverage made. The fermentation container 12 may have a size less than a size of inner space S1 of the fermentation tank 112.

The fermentation container 12 may be inserted into and accommodated in the fermentation tank 112 in a state in which the ingredients are contained in the fermentation container 12. The fermentation container 12 may be inserted into the fermentation tank 112 and then accommodated in the fermentation tank 112 in a state in which the fermentation lid 107 is opened.

The fermentation lid 107 may seal the fermentation tank 112 after the fermentation container 12 is inserted into the fermentation tank 112. The fermentation container 12 may assist fermentation of the ingredients in a state in which the fermentation container 12 is accommodated in the inner space S1 sealed by the fermentation container 112 and the fermentation lid 107. The fermentation container 12 may be expanded by pressure therein during the making of the beverage. The fermentation container 12 may be pressed by air within the fermentation tank 112 when the beverage contained in the fermentation container 12 is dispensed, and the air may be supplied between the inner surface of the fermentation tank 112 and the fermentation container 12.

The fermentation tank 112 may be disposed in the fermentation case 160. The fermentation tank 112 may have an outer circumferential surface and an outer bottom surface, which may be spaced apart from an inner surface of the fermentation case 160. The outer circumferential surface of the fermentation tank 112 may be spaced apart from an inner circumference of the fermentation case 160, and the outer bottom surface of the fermentation tank 112 may be spaced apart from an inner bottom surface of the fermentation case 160.

The insulation (not shown) may be provided between the fermentation case 160 and the fermentation tank 112. The insulation may be disposed in the fermentation case 160 to surround the fermentation tank 112. Thus, a temperature of the fermentation tank 112 may be maintained constant. The insulation may be made of a material, such as foamed polystyrene or polyurethane, which has a high thermal insulating performance and absorbs vibration.

The fermentation tank 112 may include a temperature sensor 16 that measures a temperature of the fermentation tank 112. The temperature sensor 16 may be mounted on the outer circumferential surface of the fermentation tank 112. The temperature sensor 16 may be disposed below an evaporator 134 wound around the fermentation tank 112.

A temperature controller 11 may change an inner temperature of the fermentation tank module 111. The temperature controller 11 may change a temperature of the fermentation tank 112. The temperature controller 11 may heat or cool the fermentation tank 112 to control a temperature of the fermentation tank 112 at an optimal temperature for fermenting the beverage.

The temperature controller 11 may include at least one of a refrigerant cycle device 13 and/or a heater 14. However, embodiments are not limited thereto. For example, the temperature controller 11 may include a thermoelement (TEM).

The refrigerant cycle device 13 may control the temperature of the fermentation tank 112 to cool the temperature of the fermentation tank 112. The refrigerant cycle device 13 may include a compressor, a condenser, an expansion mechanism, and the evaporator 134.

The evaporator 134 may contact the outer circumferential surface of the fermentation tank 112. The evaporator 134 may be provided as an evaporation tube wound around the outer circumferential surface of the fermentation tank 112. The evaporator 134 may be accommodated between the fermentation tank 112 and the insulation to cool the fermentation tank 112 insulated by the insulation.

The temperature controller 11 may further include heater 14 that heats the fermentation tank 112. The heater 14 may contact the outer bottom surface of the fermentation tank 112. The heater 14 may be provided as a heat generation heater that generates heat when power is applied. The heater 14 may be provided as a plate heater. Thus, natural convection of a fluid may be generated inside of the fermentation tank 112 by the evaporator 134 and the heater 14, and temperature distribution inside of the fermentation tank 112 and the fermentation container 12 may be uniform.

As described above, the main channels 41 and 42 may include first main channel 41 that connects the fluid supply module 5 to the ingredient supplier 3 and second main channel 42 that connects the ingredient supplier 3 to the fermentation module 1. That is, the first main channel 41 may guide a fluid, such as water supplied from the fluid supply module 5 to the ingredient supplier 3, and the second main channel 42 may guide a mixture of ingredients and the fluid, which are extracted from the ingredient supplier 3, to the fermentation module 1.

The first main channel 41 may have a first end 41*a* connected to the fluid supply module 5 and a second end connected to the ingredient supplier 3, more particularly, an inlet 31*a* of an initial ingredient receiver 31, which will be described hereinafter.

An ingredient supply valve 310 that opens and closes the first main channel 41 may be installed in the first main channel 41. The ingredient supply valve 310 may be provided in the ingredient supplier 3.

The ingredient supply valve 310 may be opened when additives accommodated in the ingredient receivers 31, 32, and 33 are input to open the first main channel 41. The ingredient supply valve 310 may also be opened when the ingredient receivers 31, 32, and 33 are cleaned to open the first main channel 41.

The second main channel 42 may have a first end connected to the main channel connecting portion 115 of the fermentation module 1 and a second end connected to the ingredient supplier 3, more particularly, an outlet 33*b* of a final ingredient receiver 33, which will be described hereinafter.

A main valve 40 that opens and closes the second main channel 42 may be installed in the second main channel 42. Also, a main check valve 314 that allows fluid to flow from the ingredient supplier 3 to the fermentation module 1 may be installed in the second main channel 42. That is, the main check valve 314 may prevent the fluid from flowing back to the ingredient supplier 3. The main check valve 314 may be disposed between the main valve 40 and the ingredient supplier 3 with respect to the second main channel 42.

The main valve 40 may be opened to open the second main channel 42 when fluid is supplied to the fermentation container 12. The main valve 40 may be closed to close the second main channel 42 while the fermentation tank 112 is cooled. The main valve 40 may be opened to open the second main channel 42 when air is injected into the fermentation container 12. The main valve 40 may be opened to open the second main channel 42 when ingredients are supplied into the fermentation container 1. The main valve 40 may be closed to seal the inside of the fermentation container 12 during fermentation of the ingredients. The main valve 40 may be closed to seal the inside of the fermentation container 12 when the beverage is aged and stored. The main valve 40 may be opened to open the second main channel 42 when the beverage is dispensed by the beverage dispenser 6. The beverage within the fermentation container 1 may pass through the main valve 40 to flow to the beverage dispenser 6.

The main channels 41 and 42 may be provided as one continuous channel when the fermentation and aging apparatus does not include the ingredient supplier 3. When the fermentation and aging apparatus includes the ingredient supplier 3, the fermentation and aging apparatus may further include bypass channel 43 configured to allow fluid or air to bypass the ingredient receivers 31 and 32.

The bypass channel 43 may bypass the ingredient receivers 31, 32, and 33 and then be connected to the first main channel 41 and the second main channel 42. The bypass channel 43 may have a first end 43*a* connected to the first main channel 41 and a second end 43*b* connected to the second main channel 42. The first end 43*a* of the bypass channel 43 may be connected to the first main channel 41 between the fluid supply module 5 and the ingredient supply valve 310 and the second end 43*b* may be connected to the second main channel 42 between the main valve 40 and the ingredient supplier 3.

A bypass valve 35 that opens and closes the bypass channel 43 may be installed in the bypass channel 43. The bypass valve 35 may be opened to open the bypass channel 43 when fluid supplied from the fluid supply module 5 is supplied to the fermentation container 12. The bypass valve 35 may be opened to open the bypass channel 43 when air injected from the air injector 8 is supplied to the fermentation container 12. The bypass valve 35 may be opened to open the bypass channel 43 when the bypass channel 43 is cleaned.

A bypass check valve 324 that allows fluid to flow from the first main channel 41 to the second main channel 42 may be installed in the bypass channel 43. That is, the fluid may flow only from the first main channel 41 to the second main channel 42, but may not flow in the opposite direction. The bypass check valve 324 may be disposed between the bypass valve 35 and the second main channel 42 with respect to the bypass channel 43.

When beverage is made using the fermentation and aging apparatus, ingredients used to make the beverage may include a fluid, such as water, an object to be fermented and an additive (fermentation accelerator, etc.). When beer is made using the fermentation and aging apparatus, ingredients for making the beer may include water, malt, yeast, hop, and flavoring additives, for example. The fermentation and aging apparatus may include all of the ingredient supplier 3 and the fermentation container 12. The ingredients for making the beverage may be accommodated separately in the ingredient supplier 3 and the fermentation container 12. That is, a portion of the ingredients (ingredients to be fermented) for making the beverage may be accommodated in the fermentation container 12, and the remaining ingredients may be accommodated in the ingredient supplier 3. The remaining ingredients accommodated in the ingredient supplier 3 may be supplied to the fermentation container 12 together with the fluid supplied from the fluid supply module 5 and mixed with the portion of the ingredients accommodated in the fermentation container 12.

A main ingredient (ingredients to be fermented) that is essential for making a beverage may be accommodated in the fermentation container 12, and the other ingredients or additives, for example, a fermentation accelerator added to the main ingredient may be accommodated in the ingredient supplier 3. In this case, the additives accommodated in the ingredient supplier 3 may be mixed with fluid supplied from the fluid supply module 5 and supplied to the fermentation container 12 and then mixed with the main ingredient accommodated in the fermentation container 12.

An amount of the main ingredient accommodated in the fermentation container 12 may be greater than an amount of other ingredients. For example, when beer is made, the main material may be malt of malt, yeast, hop, and flavoring additives. Also, the additive accommodated in the ingredient supplier 3 may be the other ingredients except for the malt of the ingredients for making beer, for example, yeast, hop, and flavoring additives.

According to one embodiment, the fermentation and aging apparatus may not include the ingredient supplier 3 but may include the fermentation container 12. In this case, the main ingredient may be accommodated in the fermentation container 12, and the user may directly put the additives into the fermentation container 12.

If the fermentation and aging apparatus includes both the ingredient supplier 3 and the fermentation container 12, the beverage may be more easily made. Hereinafter, a case in which the fermentation and aging apparatus includes both the ingredient supplier 3 and the fermentation container 12 will be described as an example. However, embodiments are not limited to the case in which the fermentation and aging apparatus includes both the ingredient supplier 3 and the fermentation container 12.

The ingredients within the fermentation container 12 may be fermented over time, and the beverage made in the fermentation container 12 may flow to the second main channel 42 through the main channel connecting portion 115 and also flow from the second main channel 42 to the beverage dispenser 6 to be dispensed. The ingredients that are necessary for making the beverage may be accommodated in the ingredient supplier 3, and the fluid supplied from the fluid supply module 5 may pass through the ingredient supplier 3. For example, when the beverage made in the fermentation and aging apparatus is beer, the ingredients accommodated in the ingredient supplier 3 may be yeast, hop, and flavoring additives, for example.

The ingredients accommodated in the ingredient supplier 3 may be directly accommodated into the ingredient receivers 31, 32, and 33 provided in the ingredient supplier 3. At least one ingredient receiver 31, 32, and 33 may be provided in the ingredient supplier 3. Also, a plurality of ingredient receivers 31, 32, and 33 may be provided in the ingredient supplier 3. The plurality of ingredient receivers 31, 32, and 33 may be partitioned with respect to each other.

Inlets 31a, 32a, and 33a, through which the fluid may be introduced, and outlets 31b, 32b, and 33b, through which the fluid may be discharged, may be provided in the ingredient receivers 31, 32, and 33, respectively. The fluid introduced into the inlet of one ingredient receiver may be mixed with the ingredients within the ingredient receivers and then discharged through the outlet.

The ingredients accommodated in the ingredient supplier 3 may be accommodated in ingredient containers C1, C2, and C3. The ingredient containers C1, C2, and C3 may be accommodated in the ingredient receivers 31, 32, and 33, and each of the ingredient receivers 31, 32, and 33 may be referred to as an "ingredient container mount". The ingredient containers C1, C2, and C3 may be a capsule, or a pod, for example; however, embodiments are not limited thereto.

When the ingredients are accommodated in the ingredient containers C1, C2, and C3, the ingredient supplier 3 may be configured so that the ingredient containers C1, C2, and C3 may be seated therein and withdrawn therefrom. The ingredient supplier 3 may be provided as an ingredient container kit assembly in which the ingredient containers C1, C2, and C3 are separably accommodated.

For example, a first additive, a second additive, and a third additive may be accommodated in the ingredient supplier 3. The first additive may be a fermentation accelerator, for example, yeast, the second additive may be hop, and the third additive may be a flavoring additive. The ingredient supplier 3 may include a first ingredient container mount 31 in which a first ingredient container C1 containing the first additive may be accommodated, a second ingredient container mount 32 in which a second ingredient container C2 containing the second additive may be accommodated, and a third ingredient container mount 33 in which a third ingredient container C3 containing the third additive may be accommodated.

The ingredients contained in the ingredient receivers or the ingredient containers C1, C2, and C3 may be extracted by a fluid pressure of fluid supplied from the fluid supply module 5. When the ingredients are extracted by the fluid pressure, the fluid supplied from the fluid supply module 5 to the first main channel 41 may pass through the ingredient receivers or the ingredient containers C1, C2, and C3 and then may be mixed with the ingredients, and the ingredients accommodated in the ingredient receivers or the ingredient containers C1, C2, and C3 may flow to the second main channel together with the fluid.

A plurality of different additives may be accommodated separately in the ingredient supplier 3. For example, when beer is made, the plurality of additives accommodated in the ingredient supplier 3 may be yeast, hop, and a flavoring additive, which may be accommodated separated from each other.

When the plurality of ingredient receivers is provided in the ingredient supplier 3, the plurality of ingredient receivers 31, 32, and 33 may be connected in series to each other in a flow direction of the fluid. That is, the ingredient supplier 3 may include at least one connecting channel 311 and 312 that connects the outlet of one ingredient receiver of the plurality of ingredient receivers 31, 32, and 33 to the inlet of another ingredient receiver.

Also, the plurality of ingredient receivers 31, 32, and 33 may include an initial ingredient receiver 31 and a final ingredient receiver 33. The plurality of ingredient receivers 31, 32, and 33 may further include an intermediate ingredient receiver 32.

The inlet 31a of the initial ingredient receiver 31 may be connected to the first main channel 41, and the outlet 33b of the final ingredient receiver 33 may be connected to the second main channel 42. The intermediate ingredient receiver 32 may be disposed between the first ingredient receiver 31 and the second ingredient receiver 33 in the flow direction of the fluid. The inlet 32a and the outlet 32b of the intermediate ingredient receiver 32 may be connected to different connecting channels 311 and 312 from each other.

As illustrated in FIG. 1, when three ingredient receivers are provided in the ingredient supplier 3, the outlet 31b of the initial ingredient receiver 31 may be connected to the inlet 32a of the intermediate ingredient receiver 32 through the first connecting channel 311, and the outlet 32b of the intermediate ingredient receiver 32 may be connected to the inlet 33a of the final ingredient receiver 33 through the second connecting channel 312. The fluid introduced into the inlet 31a of the final ingredient receiver 31 through the first main channel 41 may flow to the first connecting channel 311 through the outlet 31b together with the first additive accommodated in the initial ingredient receiver 31.

The fluid, which may be a mixture of water and a first additive, introduced into the inlet 32a of the intermediate ingredient receiver 32 through the first main channel 311 may flow to the second connecting channel 312 through the outlet 32b together with the second additive accommodated in the intermediate ingredient receiver 32. The fluid, which may now be a mixture of water and first and second additives, introduced into the inlet 33a of the final ingredient receiver 33 through the second main channel 312 may flow to the second connecting channel 42 through the outlet 33*b* together with a third additive accommodated in the final ingredient receiver 33. The fluid, which may now be a mixture of water and first, second, and third additives, discharged through the second main channel 42 may be guided to the main channel connecting portion 115 of the fermentation module 1 and then introduced into the fermentation container 12.

However, the configuration of the ingredient supplier is not limited thereto. For example, when the intermediate ingredient receiver is not provided, two ingredient receivers may be provided in the ingredient supplier 3. In this case, one ingredient receiver may be the initial ingredient receiver, and the other ingredient receiver may be the final ingredient receiver. The outlet of the initial ingredient receiver and the inlet of the final ingredient receiver may be connected to each other by the connecting channel.

For another example, when a plurality of the intermediate ingredient receiver is provided, four or more ingredient receivers may be provided in the ingredient supplier 3. In this case, one ingredient receiver may be the initial ingredient receiver, another ingredient receiver may be the final ingredient receiver, and the remaining ingredient receivers may be intermediate ingredient receivers. In this case, as the connection between the ingredient receivers in series is easily understood by a person skilled in the art, detailed descriptions thereof have been omitted.

As the plurality of ingredient receivers 31, 32, and 33 may be connected in series to each other, the channel configuration of the ingredient supplier 3 may be simplified. Further, as the additives contained in the ingredient containers C1, C2, and C3 may be extracted all at once, a time taken to extract the additives may decrease. Furthermore, as the user does not have to worry about a mounting order of the ingredient containers C1, C2, and C3, malfunction due to the mounting of the ingredient containers C1, C2, and C3 in an erroneous order may not occur. Also, fluid leakage in the ingredient supplier 3 may be minimized to improve reliability.

When the ingredients accommodated in the ingredient supplier 3 are accommodated in the ingredient containers C1, C2, and C3, the initial ingredient receiver 31 may be referred to as an "initial ingredient container mount", the intermediate ingredient receiver 32 may be referred to as an "intermediate ingredient container mount", and the final ingredient receiver 33 may be referred to as a "final ingredient container mount".

That is, the fermentation and aging apparatus utilizes the fermentation container 12 and the ingredient containers C1, C2 and C3, thereby accurately providing the amount of ingredients necessary to make the beverage and providing beverage having uniform quality. In addition, the fermentation container 12 and the ingredient containers C1, C2 and C3 may be easily detached and installed, thereby improving cleanliness outside/inside the apparatus.

The fluid supply module 5 may include a tank 51, a pump 52 that pumps a fluid, such as water within the tank 51, and a heater 53 that heats the fluid pumped by the pump 52. The tank 51 and the pump 52 may be connected to a tank discharge channel 55*a*, and the fluid contained in the tank 51 may be introduced into the pump 52 through the tank discharge channel 55*a*.

The pump 52 and a first end of the first main channel 41 may be connected to a supply channel 55*b*, and the fluid discharged from the pump 52 may be guided to the first main channel 41 through the supply channel 55*b*. A flow meter 56 that measures a flow rate of the fluid discharged from the tank 51 may be installed in the tank discharge channel 55*a*.

A flow rate control valve 54 that controls a flow rate of the fluid discharged from the tank 51 may be installed in the tank discharge channel 55*a*. The flow rate control valve 54 may include a step motor.

A thermistor 54*a* that measures a temperature of the fluid discharged from the tank 51 may be installed in the tank discharge channel 55*a*. The thermistor 54*a* may be built into the flow rate control valve 54.

A check valve 59 that prevents the fluid from flowing back to the pump 52 may be installed in the supply channel 55*b*. Also, the heater 53 may be installed in the supply channel 55*b*. A thermal fuse 58 that interrupts a circuit to cutoff current applied to the heater 53 when a temperature is high may be installed in the heater 53.

The fluid supply module 5 may further include a safety valve 53*a*. The safety valve 53*a* may communicate with an inside of a heater case of the heater 53. The safety valve 53*a* may restrict a maximum inner pressure of the heater case. For example, the safety valve 53*a* may restrict the maximum inner pressure of the heater case to a pressure of about 3.0 bar.

The fluid supply module 5 may further include a temperature sensor 57 that measures a temperature of the fluid passing through the heater 53. The temperature sensor 57 may be installed in the heater 53. Alternatively, the temperature sensor 57 may be disposed at a portion of the supply channel 55*b* behind the heater 53 in the flow direction of fluid. Also, the temperature sensor 57 may be installed in the first main channel 41.

When the pump 52 is driven, the fluid within the tank 51 may be introduced into the pump 52 through the tank discharge channel 55*a*. The fluid discharged from the pump 52 may be heated in the heater 53 while flowing through the supply channel 55*b* and then be guided to the first main channel 41.

The beverage dispenser 6 may be connected to the second main channel 42. The beverage dispenser 6 may include a dispenser 62 that dispenses a finished beverage and a beverage dispensing channel 61 that connects to the dispenser 62 to the second main channel 42.

The beverage dispensing channel 61 may have a first end (connecting portion) 61*a* connected between the main check valve 314 and the main valve 40 with respect to the second main channel 42 and a second end connected to the dispenser 62. A beverage dispensing valve 64 that opens and closes the beverage dispensing channel 61 may be installed in the beverage dispensing channel 61.

The beverage dispensing valve 64 may be opened to open the beverage dispensing channel 61 when the beverage is dispensed. The beverage dispensing valve 64 may be opened to open the beverage dispensing channel 61 when residual fluid is removed. The beverage dispensing valve 64 may be opened to open the beverage dispensing channel 61 when the beverage dispenser is cleaned.

An anti-foaming portion (not shown) may be provided in the beverage dispensing channel 61, and an amount of foam of the beverage flowing from the second main passage 42 to the beverage dispensing channel 61 may be minimized while passing through the anti-foaming portion. A mesh that filters the foam may be provided in the anti-foaming portion (not shown).

When the beverage is dispensed, the beverage dispensing valve 64 may be opened. When the beverage is not dispensed, the beverage dispensing valve 64 may be maintained in a closed state.

Gas discharger 7 may be connected to the fermentation module 1 to discharge gas generated in the fermentation container 12. The gas discharger 7 may include a gas discharge channel 71 connected to the fermentation module 1, a gas pressure sensor 72 installed in the gas discharge channel 71, and a gas discharge valve 73 connected upstream of the gas pressure sensor 72 in the gas discharge channel 71 in a gas discharge direction.

The gas discharge channel 71 may be connected to the fermentation module 1, more particularly, the fermentation lid 107. A gas discharge channel connecting portion 121 to which the gas discharge channel 71 may be connected may be provided in the fermentation lid 107.

Gas within the fermentation container 12 may flow into the gas discharge channel 71 and the gas pressure sensor 72 through the gas discharge channel connecting portion 121. The gas pressure sensor 72 may detect a pressure of the gas discharged to the gas discharge channel 71 through the gas discharge channel connecting portion 121 within the fermentation container 12.

The gas discharge valve 73 may be opened when air is injected into the fermentation container 12 by the air injector 8. The fermentation and aging apparatus may uniformly mix the malt with the fluid by injecting air into the fermentation container 12. Foam generated in the liquid malt may be discharged from an upper portion of the fermentation container 12 to the outside through the gas discharge channel 71 and the gas discharge valve 73. The gas discharge valve 73 may be opened during the fermentation operation and then closed.

The gas discharger 7 may further include a safety valve 75 connected to the gas discharge channel 71. The safety valve 75 may be connected upstream of the gas pressure sensor 72 in the gas discharge channel 71 in the gas discharge direction. The safety valve 75 may restrict a maximum pressure of the fermentation container 12 and the gas discharge channel 71. For example, the safety valve 75 may restrict the maximum pressure of the fermentation container 12 and the gas discharge channel 71 to a pressure of about 3.0 bar.

The gas discharger 7 may further include a pressure release valve 76. The pressure release valve 76 may be connected to the gas discharge channel 71. The pressure release valve 76 and the gas discharge valve 73 may be selectively opened/closed. The gas discharge channel 71 may be branched to be respectively connected to the gas discharge valve 73 and the pressure release valve 76.

A noise reducing device 77 may be mounted on the pressure release valve 76. The noise reducing device 77 may include at least one of an orifice structure or a muffler structure, for example.

Even though the pressure release valve 76 is opened, an inner pressure of the fermentation container 12 may gradually decrease due to the noise reducing device 77. When fermentation of the beverage progresses, the pressure release valve 76 may be opened to release the pressure in a state in which the inner pressure of the fermentation container 12 increases. The noise reducing device 77 may effectively reduce noise generated due to a difference in pressure between the inside and outside of the fermentation container 12. The pressure release valve 76 may be open/close-controlled in a fermentation operation with relatively high internal pressure. That is, the fermentation and aging apparatus may effectively discharge unnecessary gas generated in the fermentation operation through the gas discharger 7.

The air injector 8 may be connected to the supply channel 55b or the first main channel 41 to inject air. Hereinafter, for convenience of description, a case in which the air injector 8 is connected to the supply channel 55b will be described as an example.

The air injector 8 may be connected to an opposite side of sub channel 91, which will be described hereinafter, with respect to the heater 53. The air injected by the air injector 8 may pass through the heater 53 to flow to the sub channel 91 together with residual fluid within the heater 53. Thus, residual fluid within the heater 53 may be removed to maintain a clean state of the heater 53.

Alternatively, air injected from the air injector 8 to the first main channel 41 may successively pass through the bypass channel 43 and the second main channel 42 and then be injected into the fermentation container 12. Thus, stirring or aeration may be performed in the fermentation container 12.

Alternatively, air injected from the air injector 8 to the first main channel 41 may be guided to the ingredient supplier 3 to flow to the ingredient container mounts 31, 32, and 33. Residual fluid or residue within the ingredient containers C1, C2, and C3 or the ingredient container mounts 31, 32, and 33 may flow to the second main channel 42 due to air injected by the air injector 8. The ingredient containers C1, C2, and C3 and the ingredient container mounts 31, 32, and 33 may be cleanly maintained by the air injected by the air injector 8.

The air injector 8 may include an air injection channel 81 connected to the supply channel 55b or the first main channel 41 and an air pump 82 connected to the air injection channel 81. The air pump 82 may pump air to the air injection channel 81. An air injection check valve 83 that prevents fluid flowing to the supply channel 55b by the pump 52 from being introduced into the air pump 82 through the air injection channel 81 may be installed in the air injection channel 81.

The air injector 8 may further include an air filter 82a. The air filter 82a may be provided in a suction portion of the air pump 82, and thus, external air may be suctioned into the air pump 82 by passing through the air filter 82a. Thus, the air pump 82 may inject clean air into the air injection channel 81. That is, as the fermentation and aging apparatus includes the air injector 8, it is possible to smoothly supply air necessary for growing microorganisms during the fermentation operation of the beverage.

The air controller 15 may control a pressure between the inner wall of the fermentation tank 112 and the outer surface of the fermentation container 12. The air controller 15 may supply air into a space between the fermentation container 12 and the fermentation tank 112. On the other hand, the air controller 15 may exhaust the air within the space between the fermentation container 12 and the fermentation tank 112 to the outside.

The air controller 15 may include an air supply channel 154 connected to the fermentation module 1, and an exhaust channel 157 connected to the air supply channel 154 to exhaust the air to the outside. The air supply channel 154 may have a first end connected to the first main channel 41 and a second end connected to the fermentation module 1.

The air supply channel 154 may be connected to the fermentation module 1, more particularly, the fermentation lid 107. An air supply channel connecting portion 117 to which the air supply channel 154 may be connected may be provided in the fermentation module 1. The air supply channel connecting portion 117 may communicate with the space between the inner wall of the fermentation tank 112 and the outer surface of the fermentation container 12.

The air injected from the air injector 8 to the first main channel 41 may be guided between the outer surface of the fermentation container 12 and the inner wall of the fermentation tank 112 through the air supply channel 154. The air injector 8 may function as an air supplier that supplies air into the space between the fermentation container 12 and the fermentation tank 112 together with the air supply channel 154.

As described above, the air supplied into the fermentation tank 112 may press the fermentation container 12 between the outer surface of the fermentation container 12 and the inner wall of the fermentation tank 112. The beverage within the fermentation container 12 may be pressed by the fermentation container 12 pressed by the air. When the main valve 40 and the beverage dispensing valve 64 are opened, the beverage may pass through the main channel connecting portion 115 to flow to the second main channel 42. The beverage flowing from the fermentation container 12 to the second main channel 42 may be dispensed to the outside through the beverage dispenser 6.

The air pump 82 may supply air so that a predetermined pressure occurs between the fermentation container 12 and the fermentation tank 112. Thus, a pressure at which the beverage within the fermentation container 12 is easily dispensed may occur between the fermentation container 12 and the fermentation tank 112.

The air pump 82 may be maintained in an off state while the beverage is dispensed. When the beverage is completely dispensed, the air pump 82 may be driven for a next beverage dispensing and then stopped.

Thus, when the beverage is finished, the fermentation and aging apparatus may dispense the beverage within the fermentation container 12 to the beverage dispenser 6 in a state in which the fermentation container 1 is disposed within the fermentation module 1 without withdrawing the fermentation container 12 to the outside of the fermentation module 1.

The air controller 15 may include a separate air supply pump with respect to the air injector 8. In this case, the air supply channel 154 may be connected to the air supply pump, but may not be connected to the first main channel 41. However, injection of air into the fermentation container 12 by the air pump 82 and the supplying of air into the space between the fermentation container 12 and the fermentation tank 112 may be combined with each other to realize a compact product and reduce manufacturing costs.

The exhaust channel 157 may function as an air exhaust passage, through which the air between the fermentation container 12 and the fermentation tank 112 may be exhausted to the outside, together with a portion of the air supply channel 154. The exhaust channel 157 may be disposed outside of the fermentation module 1. The exhaust channel 157 may be connected to a portion of the air supply channel 154, which is disposed outside of the fermentation tank 112.

The air supply channel 154 may include a first channel connected between a connecting portion 157a connected to the first main channel 41 and the exhaust channel 157 and a second channel connected between the connecting portion 154a connected to the exhaust channel 157 and the air supply channel connecting portion 117. The first channel may be an air supply channel that guides the air pumped by the air pump 82 to the second channel. Also, the second channel may be an air supply and exhaust-combined channel that supplies the air passing through the air supply channel into the space between the fermentation tank 112 and the fermentation container 12 or guides the air discharged from the space between the fermentation tank 112 and the fermentation container 12 the connecting channel 157.

The exhaust channel 157 may be connected to an exhaust valve 156 that opens and closes the exhaust channel 157. The exhaust valve 156 may be opened so that the air between the fermentation container 12 and the fermentation tank 112 may be exhausted to the outside when the fermentation container 12 is expanded while the beverage is made. The exhaust valve 156 may be opened when the fluid is supplied by the fluid supply module 5. The exhaust valve 156 may be opened when the air is injected by the air injector 8.

The exhaust valve 156 may be opened so that the air between the fermentation container 12 and the fermentation tank 112 may be exhausted when the beverage within the fermentation container 12 is completely dispensed. The user may take the fermentation container 12 out of the fermentation tank 112 when the beverage is completely dispensed. This is done because safety accidents occur when the inside of the fermentation tank 112 is maintained at a high pressure. The exhaust valve 156 may be opened when the beverage within the fermentation container 12 is completely dispensed.

The air controller 15 may further include an air supply valve 159 that restricts the air pumped by the air pump 82 and supplied between the fermentation container 12 and the fermentation tank 112. The air supply valve 159 may be installed in the air supply channel 154. That is, the air supply valve 159 may be installed between the connecting portion 154a of the first main channel 41 and the connecting portion 157a of the exhaust channel 157 in the air supply channel 154.

The sub channel 91 may connect the fluid supply module 5 to the beverage dispenser 6. That is, the sub channel 91 may have a first end 91a connected to the supply channel 55b and a second end 91b connected to the beverage dispensing channel 61.

The sub channel 91 may be connected between the pump 52 and the heater 53 with respect to the supply channel 55b. Also, the sub channel 91 may be connected to the connecting portion 61a of the second main channel 42 and the beverage dispensing valve 64 with respect to the beverage dispensing channel 61.

The fluid supplied by the pump 52 and the air pumped by the air pump 82 may be guided to the beverage dispensing channel 61 through the sub channel 91 and then may be dispensed to the dispenser 62. Thus, residual fluid or beverage remaining in the beverage dispenser 6 may be removed.

A sub valve 92 that opens and closes the sub channel 91 may be installed in the sub channel 91. The sub valve 92 may be opened to open the sub channel 91 when the beverage is dispensed, or cleaning is performed.

A sub check valve 93 that prevents the beverage in the beverage dispensing channel 61 from flowing back to the fluid supply module 5 may be installed in the sub channel 91. The sub check valve 93 may be disposed between the sub valve 92 and the beverage dispensing channel 61 with respect to the sub channel 91.

The sub channel 91 may function as a residual fluid removing channel of the fluid supply module 5. For example, when the air pump 82 is turned on in a state in which the air supply valve 159, the bypass valve 35, and the ingredient supply valve 310 are closed, the sub valve 92 is opened, and the air injected into the air injection channel 81 may pass through the heater 53 to flow to the sub channel 91. Then, the air may pass through the sub valve 92 to flow to the beverage dispensing channel 61 and then be dispensed to the dispenser 62. In this operation, the air may be dispensed together with fluid from the fluid supply module 5, more particularly, the residual fluid remaining in the heater 53 and the supply channel 55*b* so that residual fluid may be removed.

In addition, the sub channel 91 may function as a cleaning channel. That is, a beverage may be partially dispensed by the dispenser 62, and when a long period of time has elapsed before a next beverage dispensing, fluid may flow to the sub channel 91 to clean the dispenser 62 before the next beverage dispensing is performed.

Figure 2:
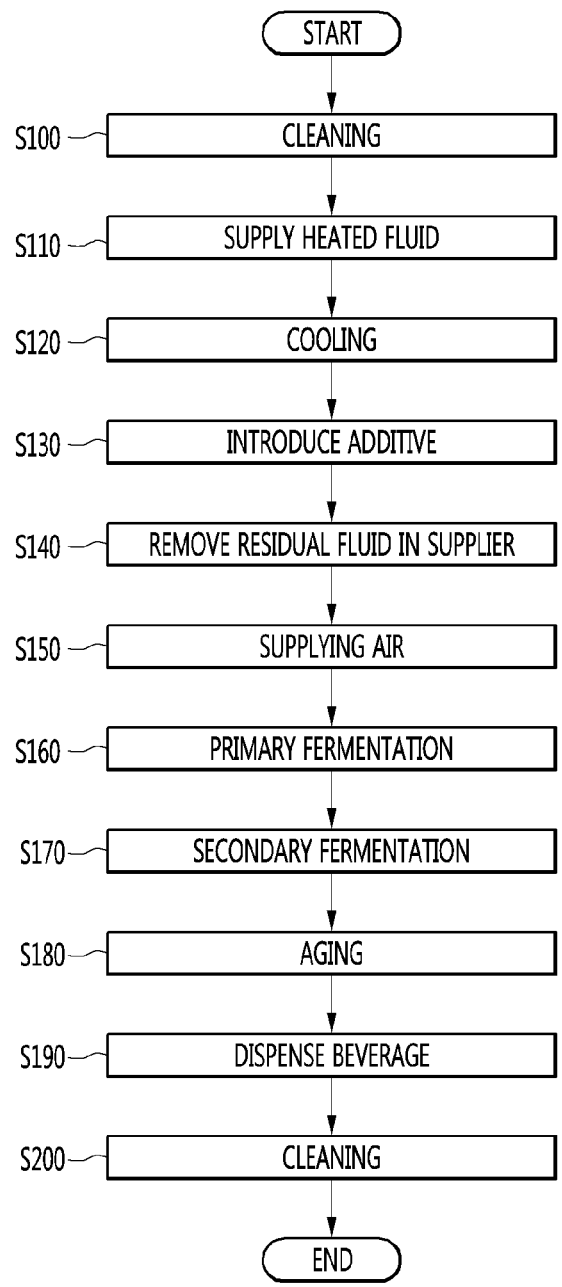
FIG. 2 is a flowchart of a method for controlling a fermentation and aging apparatus according to an embodiment.

FIG. 2 is a flowchart of a method for controlling a fermentation and aging apparatus according to an embodiment. The fermentation and aging apparatus according to this embodiment may include cleaning operations (S100 and S200) for cleaning the channels. The cleaning operations (S100 and S200) may be separately performed with respect to a beverage making operation. The cleaning operations (S100 and S200) may be performed before and after the beverage making operation.

Also, the cleaning operations (S100 and S200) may be performed by a user input during the beverage making operation. In this case, like a primary fermentation operation (S160) or a secondary fermentation operation (S170), which will be described hereinafter, the cleaning operations (S100 and S200) may be performed while the channel connected to the fermentation module 1 is closed, and the ingredients are not contained in the ingredient suppler 3.

The cleaning operations (S100 and S200) may be performed in a state in which the ingredient containers are accommodated in the ingredient supplier 3, and the fermentation container 12 is accommodated in the fermentation module 1. The user may input a cleaning command through an input unit 420 (referring to FIG. 3), a remote controller, or a portable terminal. A controller 460 may control the fermentation and aging apparatus to perform the cleaning operations (S100 and S200) according to the input of the cleaning command.

Also, the user may input a beverage making command through the input unit 420, a remote controller, or a portable terminal. The controller 460 may control the fermentation and aging apparatus to perform the cleaning operations (S100 and S200) before and after the beverage making operation according to the input of the beverage making operation.

The controller 460 may supply a fluid, such as water of the tank 51 to the inner channels and the ingredient supplier 3 in the cleaning operation. The supplied fluid may be discharged to the outside through the dispenser 62 together with foreign matter or residue present in the channels and the ingredient supplier 3.

In the fermentation and aging apparatus, the cleaning operation may be performed during a predetermined cleaning time. After the predetermined cleaning time, the cleaning operation may be completed. As the cleaning operation is provided, it is possible to prevent internal contamination or microorganism propagation of the fermentation and aging apparatus.

The beverage making operation of making a beverage may be performed in the fermentation and aging apparatus according to this embodiment. The user may seat the fermentation container 12 on or in the fermentation module 1 for the beverage making operation. In this case, some (for example, malt) of ingredients may be received in the fermentation container 12. The malt may be received in the form of malt oil.

The user may insert the plurality of ingredient containers C1, C2, and C3 into the ingredient supplier 3 before or after the fermentation container 12 is seated. The user may input the beverage making command through the input unit 420, the remote controller, or the mobile terminal. The controller 460 may control the fermentation and aging apparatus to perform the beverage making operation according to the input of the beverage making command.

The beverage making operation may include a fluid supply operation (S110). The fluid supply operation (S110) may be a liquid malt formation operation of mixing the malt in the fermentation container 12 with heated fluid to form liquid malt.

The controller 460 may turn on the pump 52 to introduce the fluid from the tank 51 into the fermentation container 12, in the fluid supply operation (S110). According to an embodiment, to introduce heated fluid into the fermentation container 12, the fluid supply module 5 may further include the heater 53. The fluid discharged from the tank 51 may pass through the pump 52, may flow to the heater 53, and may be heated by the heater 53. Fluid heated by the heater 53 may be introduced into the fermentation container 12 through a channel between the fluid supply module 5 and the fermentation module 1. The heated fluid introduced into the fermentation container 12 may be mixed with the malt contained in the fermentation container 12, and the malt in the fermentation container 12 may be mixed with the fluid and gradually diluted. As the heated fluid is supplied to the fermentation container 12, the malt accommodated in the fermentation container 12 may be quickly uniformly mixed with the heated fluid.

The controller 460 may perform the fluid supply operation (S110) until an amount of accumulated fluid detected by the flow meter 56 reaches a target flow rate, and when the amount of accumulated fluid detected by the flow meter 56 reaches the target flow rate, the fluid supply operation (S110) may be ended. When the fluid supply operation (S110) is complete, the controller 460 may turn off the pump 52 and the heater 53.

The beverage making operation may include a fermentation tank cooling operation (S120). When the fluid supply operation (S110) is complete, the fermentation tank cooling operation (S120) for cooling the fermentation tank 112 or the fermentation container 12 may be performed.

The controller 460 may control the temperature controller 11 to cool the fermentation container 12. The controller 460 may control the refrigerant cycle device 3 to cool the fermentation container 12. When the refrigerant cycle device 3 is driven, the fermentation container 12 may be gradually cooled, and also, the liquid malt accommodated in the fermentation container 12 may be cooled. The controller 460 may control the refrigerant cycle device 13 according to the temperature detected by the temperature sensor 16 installed in the fermentation module 1.

The beverage making operation may include an additive introducing operation (S130). The fermentation and aging apparatus may perform the additive introducing operation (S130) while performing the cooling operation (S120). For example, the fermentation and aging apparatus may perform the additive introducing operation (S130), when the temperature sensed by the temperature sensor 16 reaches a specific temperature value higher than the cooling temperature set for the cooling operation (S120).

In the additive introducing operation (S130), ingredients received in the ingredient supplier 3 may be introduced into the fermentation container 12. The controller 460 may turn on the pump 52. When the pump 52 is turned on, the fluid in the tank 51 may be introduced into the ingredient supplier 3 by passing through the pump 52 and a channel between the fluid supply module 5 and the ingredient supplier 3. Fluid introduced into the ingredient supplier 3 may be mixed with the ingredient contained in the ingredient supplier 3 and introduced into the fermentation container 12 together with the ingredient.

The controller 460 may complete the additive introducing operation (S130) when the accumulated flow rate detected by the flow meter 56 reaches the additive introduction target flow rate from a start of the additive introducing operation (S130). When the additive introducing operation (S130) is completed, the controller 460 may turn off the pump 52.

The beverage making operation may include an ingredient supplier residual fluid removing operation (S140). When the additive introducing operation (S130) is complete, the ingredient supplier residual fluid removing operation (S140) of removing residual fluid from the ingredient supplier 3 may be performed.

In the ingredient supplier residual fluid removing operation (S140), the controller 460 may turn on the air pump 82. When the air pump 82 is turned on, air may be introduced into the ingredient supplier 3 through a channel between the air pump 82 and the ingredient supplier 3. The air introduced into the ingredient supplier 3 may push residual fluid in the ingredient supplier 3 into a channel between the ingredient supplier 3 and the fermentation module 1. The air flowing into the channel may be introduced into the fermentation container 12 together with the residual fluid. Accordingly, ingredients and fluid, which are not extracted, but remain in the ingredient supplier 3, may be entirely introduced into the fermentation container 12.

The controller 460 may turn on the air pump 82 for a predetermined residual fluid removal time and may end the ingredient supplier residual fluid removing operation (S140) after the predetermined residual fluid removal time has elapsed. When the ingredient supplier residual fluid removing operation (S140) is complete, the controller 460 may turn on the air pump 82.

The beverage making operation may further include an air supplying operation (S150). The fermentation and aging apparatus may complete the cooling operation (S120) when the temperature sensed by the temperature sensor 16 is equal to or less than a cooling temperature at least one time after the cooling operation (S120) is commenced and the refrigerant cycle device is turned on. The fermentation and aging apparatus may perform the air supplying operation (S150) of supplying air into the fermentation container 12 to mix liquid malt, after the cooling operation (S120) is completed.

In the air supplying operation (S150), the controller 460 may turn on the air pump 82. While the air pump 82 is in an ON state, the air may be introduced into the fermentation container 12 by passing through the channel between the air pump 82 and the fermentation module 1. The air introduced into the fermentation container 12 as described above may collide with the liquid malt to help the malt be more uniformly mixed with the heated fluid. In addition, the air colliding with the liquid malt may supply oxygen to the liquid malt. In other words, stirring and aeration may be performed.

The controller 460 may turn on the air pump 82 and may mix the air with the liquid malt for a predetermined mixing time, and may complete the air supplying operation (S150) when the predetermined mixing time has elapsed after the air pump 82 is turned on. In the air supplying operation (S150), the controller 460 may turn off the air pump 82.

The beverage making operation may include the fermentation operation (S160 and S170). The fermentation operation may include the primary fermentation operation (S160) and the secondary fermentation operation (S170).

The controller 460 may control the temperature controller 11 such that the temperature measured by the temperature sensor 16 is maintained at a primary fermentation target temperature in the primary fermentation operation. The controller 460 may periodically open or close the gas discharge valve 73 that opens or closes a channel between the fermentation container 12 and the outside, and may store the pressure sensed by the gas pressure sensor 72 in a memory 450 while the gas discharge valve 73 is closed. The controller 460 may complete the primary fermentation operation (S160), when a variation in pressure periodically sensed by the gas pressure sensor exceeds a primary fermentation reference pressure variation.

The controller 460 may commence the secondary fermentation operation (S170) after the primary fermentation operation (S160) is completed. The controller 460 may control the temperature controller 11 such that the temperature measured by the temperature sensor 16 becomes a secondary fermentation target temperature in the secondary fermentation operation (S170). The secondary fermentation target temperature may be equal to the first fermentation target temperature; however, embodiments are not limited thereto.

The controller 460 may open and close the gas discharge valve 73 based on the inner pressure of the fermentation tank 112 after the secondary fermentation operation (S170) is commenced. When the variation in the pressure sensed by the gas pressure sensor 72 exceeds a secondary fermentation pressure variation, or when the secondary fermentation progress time exceeds the predetermined secondary fermentation time, the controller 460 may determine that the secondary fermentation is completed and may end the secondary fermentation operation (S170).

Alternatively, the controller 460 may open and close the gas discharge valve 73 such that the inner pressure of the fermentation tank 112 is maintained to be within a secondary fermentation pressure range for the predetermined secondary fermentation time. The controller 460 may complete the secondary fermentation operation (S170) when the predetermined secondary fermentation time has elapsed. That is, the fermentation and aging apparatus may naturally produce carbonic acid in the beverage through the secondary fermentation operation.

The beverage making operation may include an aging operation (S180). When the primary fermentation operation (S160) and the secondary fermentation operation (S170) are completed, the aging operation (S180) may be performed.

The controller 460 may stand by for an aging time in the aging operation (S180), and may control the temperature controller 11 such that the temperature of the beverage is maintained between an upper limit and a lower limit of a target aging temperature for the aging time.

When the aging time has elapsed, the beverage is completely made. However, if necessary, the aging operation (S180) may be omitted and the beverage making may be completed when the secondary fermentation operation (S170) is completed.

Figure 3:
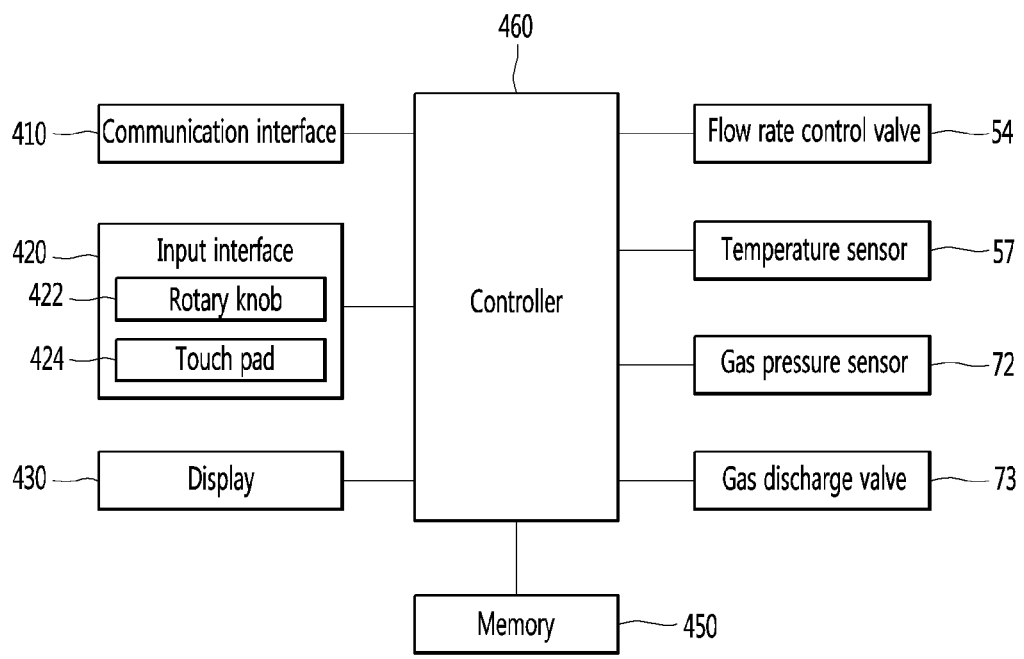
FIG. 3 is a schematic block diagram for controlling a fermentation and aging apparatus according to an embodiment.

The controller 460 may display that the beverage making is completed, through a display 430 (see FIG. 3). In addition, the controller 460 may inform the user of information on the beverage making operation through a communication unit 410 or the display 430. Therefore, the user may conveniently check the beverage making operation and easily make the beverage through the fermentation and aging apparatus by themselves.

The controller 460 may maintain the temperature of the fermentation container 12 between an upper limit and a lower limit of a target drinking temperature until a beverage dispensing operation (S190) to be described hereinafter is completed.

According to an embodiment, the fermentation and aging apparatus may further perform the beverage dispensing operation (S190) of dispensing a beverage after the beverage is completely made. In the beverage dispensing operation (S190), the user may dispense a beverage by operating the dispenser 62. When the user opens the dispenser 62, the beverage in the fermentation container 12 may be dispensed through the dispenser 62 after passing through the channel between the fermentation module 1 and the dispenser 62.

The user may dispense the beverage at least once through the dispenser 62. In other words, the beverage dispensing operation may be performed at least once, and the controller 460 may determine whether the beverage dispensing is completed by using information, such as a time during which the dispenser 62 is opened.

When the controller 460 determines that all of the beverage in the fermentation container 12 is dispensed, and thus, the beverage dispensing operation is completed, the controller 460 may further perform a cleaning operation (S200) after the beverage making operation and the beverage dispensing operation. The cleaning operation (S200) may be similar to the cleaning operation (S100) before the beverage making operation.

As described above, the fermentation and aging apparatus may perform the fluid supply operation (S110) of introducing hot fluid into the fermentation container 12. Hereinafter, for convenience of description, the fluid supply operation may be referred to as a "hot fluid supply operation".

During the hot fluid supply operation, a temperature of fluid introduced into the fermentation container 12 through the heater 53 may vary according to the temperature of fluid accommodated in the tank 51, and the temperature of a space in which the fermentation and aging apparatus is disposed, for example.

That is, the temperature of fluid introduced into the fermentation container 12 may be different from a target temperature in the hot fluid supply operation. In this case, an object to be fermented, for example, malt, which is accommodated in the fermentation container 12, and fluid may not be effectively mixed or a total time required to make the beverage may be increased or decreased, thereby lowering a quality of the made beverage.

A configuration and operation of a beverage maker according to embodiments for solving the above-described problems will be described with reference to the following drawings.

FIG. 3 is a schematic block diagram illustrating components for controlling a fermentation and aging apparatus according to an embodiment. The components for controlling the fermentation and aging apparatus, which are illustrated in FIG. 3, are not essential components to realize the fermentation and aging apparatus. Accordingly, the fermentation and aging apparatus according to embodiments may include more or less components.

Referring to FIG. 3, the fermentation and aging apparatus may include communication interface 410 to communicate with a terminal, such as a smart phone or a tablet PC, for example, or a server, for example. For example, the controller 460 may receive a request for performing a function of making a beverage from a terminal of the user or recipe information through the communication interface 410. In addition, the controller 460 may transmit various pieces of information, such as an operation of the fermentation and aging apparatus, a beverage making state, and a storage state of the beverage, for example, to the terminal or the server through the communication interface 410.

The communication interface 410 may include a module to support at least one of various wireless/wired communication schemes, which are well known. For example, the communication interface 410 may include a short-range wireless communication module, such as Bluetooth or Near Field Communication (NFC), or a wireless Internet module, such as a wireless local area network (WLAN) module. For example, the NFC module may obtain recipe information corresponding to a beverage preparation pack or a beverage preparation kit from a NFC tag as the NFC tag included in the beverage preparation pack or the beverage preparation kit approaches within a predetermined distance.

The input interface 420 may be configured to receive various requests or commands from a user. For example, the input interface 420 may include a rotary knob 422, a touch pad 424 (or a touch screen), other buttons, and/or a microphone, for example. The controller 460 may receive a request for execution of a beverage making function, recipe information, and control commands for various operations of the fermentation and aging apparatuses through the input interface 420, for example.

According to an embodiment, the fermentation and aging apparatus may further include a code recognizer to obtain recipe information. For example, the code recognizer may be implemented with a quick response (QR) code recognizer to recognize a QR code included in a beverage preparation pack or a beverage preparation kit, and obtain recipe information corresponding to the recognized QR code.

The display 430 may output various pieces of information associated with an operation or state of the fermentation and aging apparatus and various pieces of information associated with the beverage which is being made or stored in the fermentation and aging apparatus. The display 430 may be implemented with a liquid crystal display (LCD), a light emitting diode (LED), and/or an organic light emitting diode (OLED) display, for example.

For example, the display 430 may output the information in a graphic form or a text form. The fermentation and aging apparatus may further include a speaker to output the information in the form of a voice. The controller 460 may output the information through various combinations of a graphic, a text, and/or voice using the display 430 and the speaker.

The memory 450 may store various pieces of information or data associated with the operation of the fermentation and aging apparatus. For example, the memory 450 may store recipe information for beverages that may be made or various program data for the operation of the fermentation and aging apparatus. In addition, the memory 450 may store various graphic data associated with screens displayed through the display 430.

In addition, the memory 450 may store values for making beverages corresponding to multiple pieces of recipe information. For example, the values for making the beverages may include a cooling temperature described with reference to FIG. 2, a primary fermentation target temperature, a primary fermentation reference pressure variation, a secondary fermentation target temperature, a secondary fermentation pressure range, or a secondary fermentation time. In addition, the values for making the beverages may further include information on the target temperature in the hot fluid supply operation.

In some embodiments, the memory 450 may further store data or an algorithm for controlling a degree of opening (opening degree) of the flow rate control valve 54 based on the temperature of fluid introduced into the fermentation tank measured by the temperature sensor 57 or the target temperature.

The controller 460 may control an overall operation of the fermentation and aging apparatus. In this case, the controller 460 may refer to at least one controller. The at least one controller may be implemented in hardware, such as a CPU, an application processor, a microcomputer, an integrated circuit, and/or an application specific integrated circuit (ASIC), for example.

The controller 460 according to an embodiment may control the degree of opening of the flow rate control valve 54 based on the temperature of a fluid, such as water introduced into the fermentation tank measured through the temperature sensor 57 while the fluid supply operation (hot fluid supply operation (S110) described with reference to FIG. 2. Embodiments related thereto will be described below with reference to FIGS. 4 to 7.

In addition, the controller 460 may control the gas pressure sensor 72 in order to measure the internal pressure of the fermentation tank 12 in the fermentation operations S160 and S170. In addition, the controller 460 may discharge gas including off-flavor generated during fermentation, control internal pressure of the fermentation container 12 or control the gas discharge valve 73, in the fermentation operations (S160 and S170). Embodiments related thereto will be described hereinafter with reference to FIGS. 8 and 9.

Figure 4:
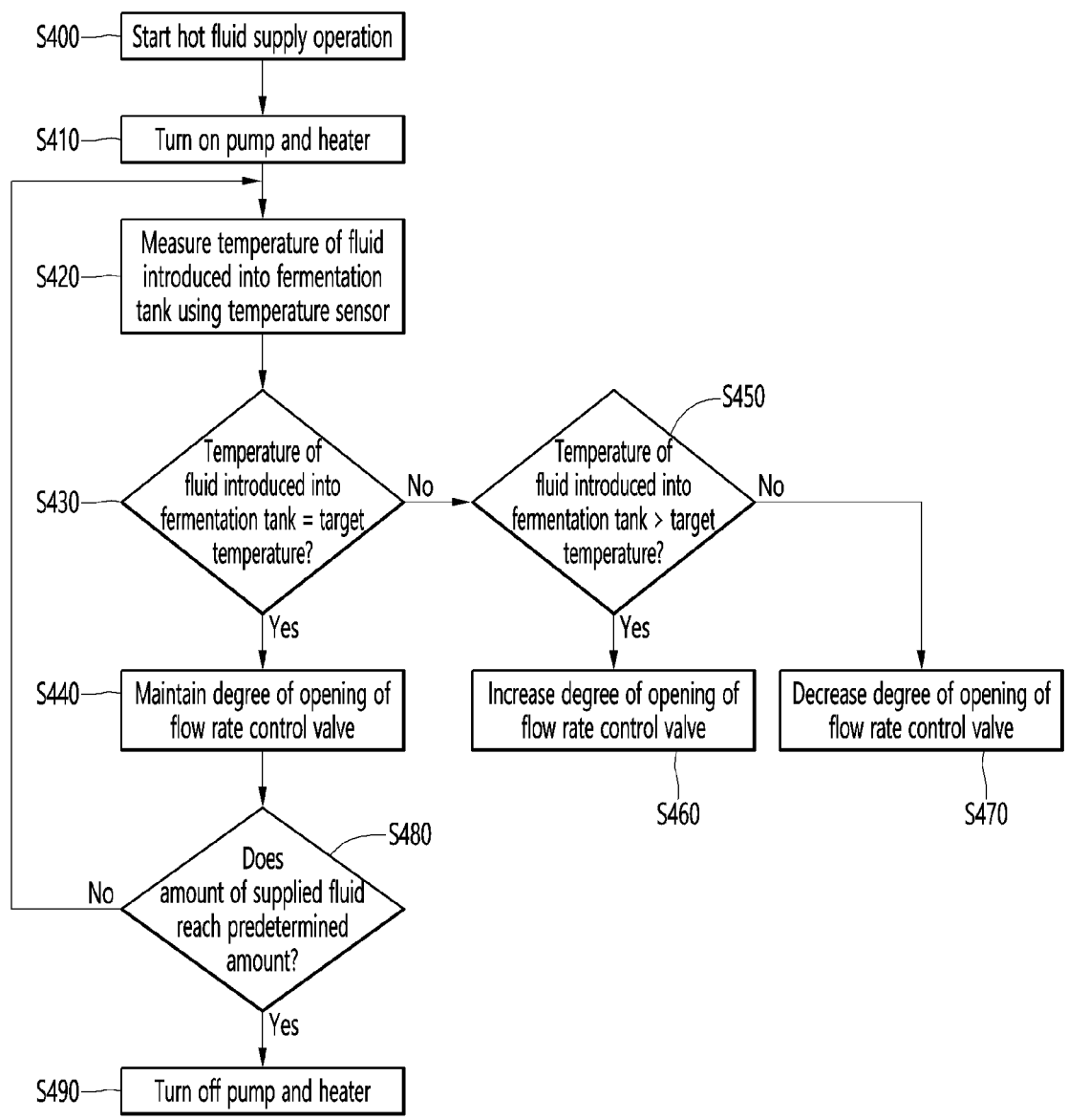
FIG. 4 is a flowchart of a control operation of a fermentation and aging apparatus according to an embodiment.
Figure 5:
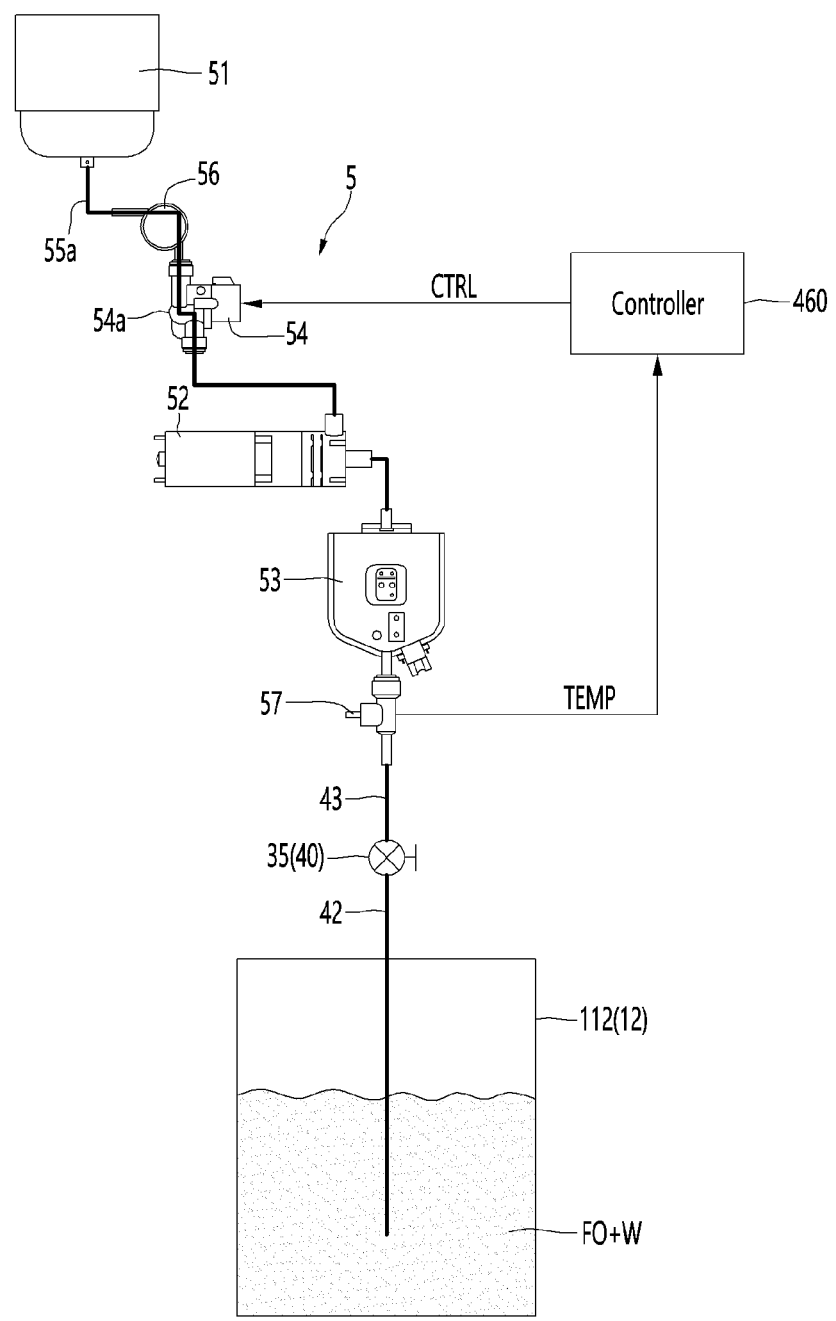
FIG. 5 is a view showing an example of the control operation of the fermentation and aging apparatus shown in FIG. 4.

FIG. 4 is a flowchart of control operation of a fermentation and aging apparatus according to an embodiment. FIG. 5 is a view showing an example of a control operation of the fermentation and aging apparatus shown in FIG. 4.

Although hot fluid, such as water is described as being introduced into the fermentation container 12 in this specification, in some embodiments, the hot fluid may be introduced into the fermentation tank 112 when the object to be fermented is directly accommodated in the fermentation tank 112. Hereinafter, in the following embodiments, the fermentation container 12 may refer to the fermentation tank 112.

Referring to FIGS. 4 and 5, the fermentation and aging apparatus may turn on the pump 52 and the heater 53 (S410), as the hot fluid supply operation among the beverage making operations starts (S400). As described above with reference to FIG. 2, the controller 460 may turn on the pump 52 and open the flow rate control valve 54 such that the fluid of the tank 51 may be introduced into the fermentation container 12, during the hot fluid supply operation.

In addition, in order to introduce hot fluid into the fermentation container 12, the controller 460 may turn on the heater 53. In this case, the fluid discharged from the tank 51 may flow to the heater 53 through the flow rate control valve 54 and the pump 52, thereby being heated in the heater 53. The fluid heated by the heater 53 may be introduced into the fermentation container 12 through the channels, such as, the bypass valve, and the main valve 42, for example, between the fluid supply module 5 and the fermentation module 1.

The fermentation and aging apparatus may measure a temperature TEMP of the fluid introduced into the fermentation tank using the temperature sensor 57 (S420). The temperature sensor 57 may be installed in the heater 53 or at an outlet side of the heater 53 (between the heater 53 and the fermentation container 12).

The controller 460 may measure the temperature of the hot fluid passing through the heater 53 (the temperature TEMP of the fluid introduced into the fermentation tank) using the temperature sensor 57. The fermentation and aging apparatus may maintain the degree of opening (the opening degree) of the flow rate control valve 54 (S440), when the measured temperature of the fluid introduced into the fermentation tank is equal to the target temperature (YES of S430).

The temperature of the fluid introduced into the fermentation tank being equal to the target temperature may include a case in which the temperature of the fluid introduced into the fermentation tank is completely equal to the target temperature but also a case in which a difference between the temperature of the fluid introduced into the fermentation tank and the target temperature is within a reference value. The target temperature may vary according to a type of beverage to be made, without being limited thereto.

The controller 460 may control (CTRL) the flow rate control valve 54 to maintain the degree of opening of the flow rate control valve 54 when the measured temperature of the fluid introduced into the fermentation tank is equal to the target temperature, thereby maintaining the flow rate of fluid passing through the heater 53. As described above, the flow rate control valve 54 may include a step motor (step-in motor), thereby changing the degree of opening (the opening degree) of the flow rate control valve 54 according to a set or predetermined step.

In contrast, when the temperature of the fluid introduced into the fermentation tank is higher than the target temperature (YES of S450), the fermentation and aging apparatus may increase the degree of opening of the flow rate control valve 54 (S460). The controller 460 may control (CTRL) the flow rate control valve 54 to increase the degree of opening of the flow rate control valve 54 when the temperature of the fluid introduced into the fermentation tank is higher than the target temperature, thereby increasing the flow rate of fluid passing through the heater 53.

As the flow rate of the fluid passing through the heater 53 increases, the temperature of the hot fluid passing through the heater 53 (the temperature of the fluid introduced into the fermentation tank) may decrease as compared to a previously measured temperature of the fluid introduced into the fermentation tank, thereby becoming close to the target temperature. In some embodiments, the temperature of the fluid introduced into the fermentation tank being higher than the target temperature may mean that the temperature of the fluid introduced into the fermentation tank is higher than the target temperature by the reference value or more.

In contrast, when the temperature of the fluid introduced into the fermentation tank is lower than the target temperature (NO of S450), the fermentation and aging apparatus may decrease the degree of opening of the flow rate control valve 54 (S470). The controller 460 may control (CTRL) the flow rate control valve 54 to decrease the degree of opening of the flow rate control valve 54 when the temperature of the fluid introduced into the fermentation tank is lower than the target temperature, thereby decreasing the flow rate of the fluid passing through the heater 53.

As the flow rate of the fluid passing through the heater 53 decreases, the temperature of the hot fluid passing through the heater 53 may increase as compared to the previously measured temperature of the fluid introduced into the fermentation tank, thereby becoming close to the target temperature. In some embodiments, the temperature of the fluid introduced into the fermentation tank being lower than the target temperature may mean that the temperature of the fluid introduced into the fermentation tank is lower than the target temperature by the reference value or more.

During the hot fluid supply operation, the fermentation and aging apparatus may calculate the amount of supplied fluid based on the flow rate measured through the flow meter 56. The fermentation and aging apparatus may continuously perform operations S420 to S470 when the calculated amount of supplied fluid does not reach a set or predetermined amount (NO of S480).

The fermentation and aging apparatus may turn off the pump 52 and the heater 53 to complete the hot fluid supply operation (S490), when the calculated amount of supplied fluid reaches the set or predetermined amount (YES of S480).

Figure 6:
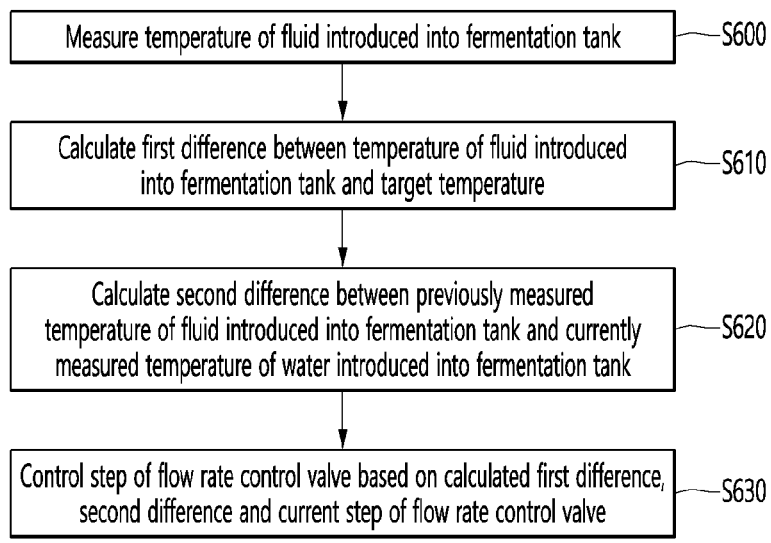
FIG. 6 is a flowchart of a control operation in which a fermentation and aging apparatus controls a degree of opening of a flow rate control valve based on a measured temperature of fluid introduced into a fermentation tank.

FIG. 6 is a flowchart of a control operation in which a fermentation and aging apparatus controls a degree of opening of a flow rate control valve based on a measured temperature of fluid introduced into a fermentation tank. Referring to FIG. 6, the fermentation and aging apparatus may measure the temperature of the fluid introduced into the fermentation tank using the temperature sensor 57 during the hot fluid supply operation (S600). Operation S600 is substantially equal to operation S420 of FIG. 4, and thus, repetitive description thereof has been omitted.

The fermentation and aging apparatus may calculate a first difference between the temperature of the fluid introduced into the fermentation tank and the target temperature (S610). In addition, the fermentation and aging apparatus may calculate a second difference between the previously measured temperature of the fluid introduced into the fermentation tank and the currently measured temperature of the fluid introduced into the fermentation tank (S620).

The fermentation and aging apparatus may control the step (the degree of opening) of the flow rate control valve 54 based on the calculated first and second differences and the current step (the current degree of opening) of the flow rate control valve 54 (S630). According to the embodiment of FIG. 6, the fermentation and aging apparatus may more effectively control the step of the flow rate control valve 54 according to change in temperature of the fluid introduced into the fermentation tank.

For example, when the currently measured temperature of the fluid introduced into the fermentation tank is lower than the target temperature but the previously measured temperature of the fluid introduced into the fermentation tank is higher than the currently measured temperature of the fluid introduced into the fermentation tank, the temperature of the fluid introduced into the fermentation tank may gradually increase to approach the target temperature. Therefore, the controller 460 may maintain the step (the degree of opening) of the flow rate control valve 54 even if the temperature of the fluid introduced into the fermentation tank is lower than the target temperature.

Similarly, when the currently measured temperature of the fluid introduced into the fermentation tank is higher than the target temperature but the previously measured temperature of the fluid introduced into the fermentation tank is lower than the currently measured temperature of the fluid introduced into the fermentation tank, the temperature of the fluid introduced into the fermentation tank may gradually decrease to approach the target temperature. Therefore, the controller 460 may maintain the step (the degree of opening) of the flow rate control valve 54 even if the temperature of the fluid introduced into the fermentation tank is higher than the target temperature.

In contrast, when the currently measured temperature of the fluid introduced into the fermentation tank is lower than the target temperature and is equal to or less than the previously measured temperature of the fluid introduced into the fermentation tank, the temperature of the fluid introduced into the fermentation tank may not approach the target temperature. Therefore, the controller 460 may decrease the step (the degree of opening) of the flow rate control valve 54.

Similarly, when the currently measured temperature of the fluid introduced into the fermentation tank is higher than the target temperature and is equal to or greater than the previously measured temperature of the fluid introduced into the fermentation tank, the controller 460 may increase the step (the degree of opening) of the flow rate control valve 54. That is, the controller 460 may more intelligently control the flow rate control valve 54 according to change in temperature of the fluid introduced into the fermentation tank. In addition, according to this embodiment, as it is possible to prevent the degree of opening of the flow rate control valve from being excessively frequently controlled, more efficient control is possible and risk of damage to the flow rate control valve may be reduced.

Figure 7:
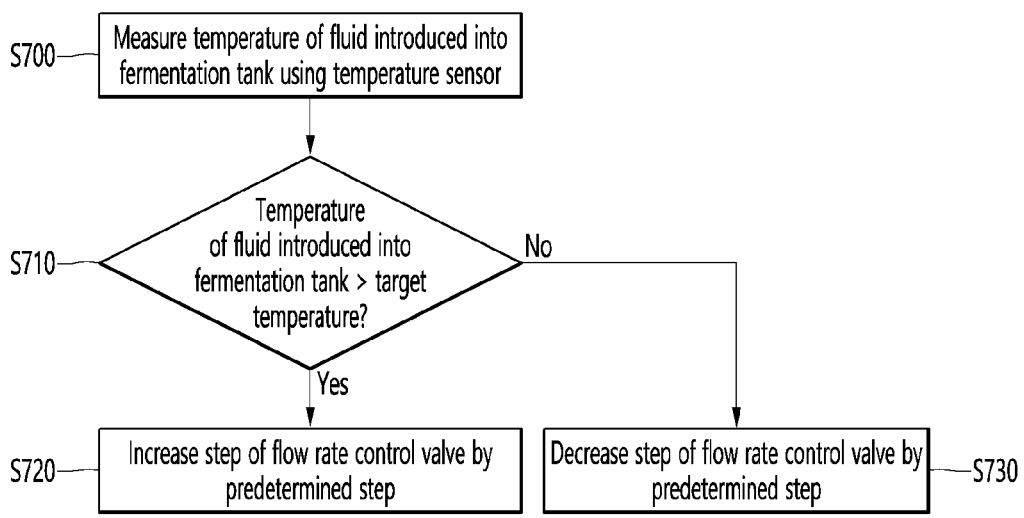
FIG. 7 is a flowchart illustrating another example of a control operation in which a fermentation and aging apparatus controls a degree of opening of a flow rate control valve based on a measured temperature of fluid introduced into a fermentation tank.

FIG. 7 is a flowchart illustrating another example of a control operation in which a fermentation and aging apparatus controls a degree of opening of a flow rate control valve based on a measured temperature of fluid introduced into a fermentation tank. Referring to FIG. 7, the fermentation and aging apparatus may measure the temperature of the fluid introduced into the fermentation tank using the temperature sensor 57 during the hot fluid supply operation (S700). Operation S700 is substantially equal to operation S420 of FIG. 4, and thus, repetitive description thereof has been omitted.

The fermentation and aging apparatus may increase the step (the degree of opening) of the flow rate control valve 54 by a preset or predetermined step (S720), when the measured temperature of the fluid introduced into the fermentation tank is higher than the target temperature (YES of S710). In contrast, when the measured temperature of the fluid introduced into the fermentation tank is lower than the target temperature (NO of S710), the fermentation and aging apparatus may decrease the step (the degree of opening) of the flow rate control valve 54 by the preset or predetermined step (S730).

That is, the controller 460 may control the step of the flow rate control valve 54 by the preset or predetermined step according to a high and low relationship between the temperature of the fluid introduced into the fermentation tank and the target temperature, thereby minimizing complexity of calculation and controlling the temperature of the fluid introduced into the fermentation tank in a simple manner.

According to the embodiments shown in FIGS. 4 to 7, the fermentation and aging apparatus may accurately control the temperature of the hot fluid introduced into the fermentation container 12 to the target temperature in the hot fluid supply operation. That is, as the temperature of the hot fluid introduced into the fermentation container 12 is maintained at the target temperature regardless of the temperature of the fluid accommodated in the tank 51 or an external temperature of the fermentation and aging apparatus, it is possible to uniformly maintain the quality of the made beverage.

Figure 8:
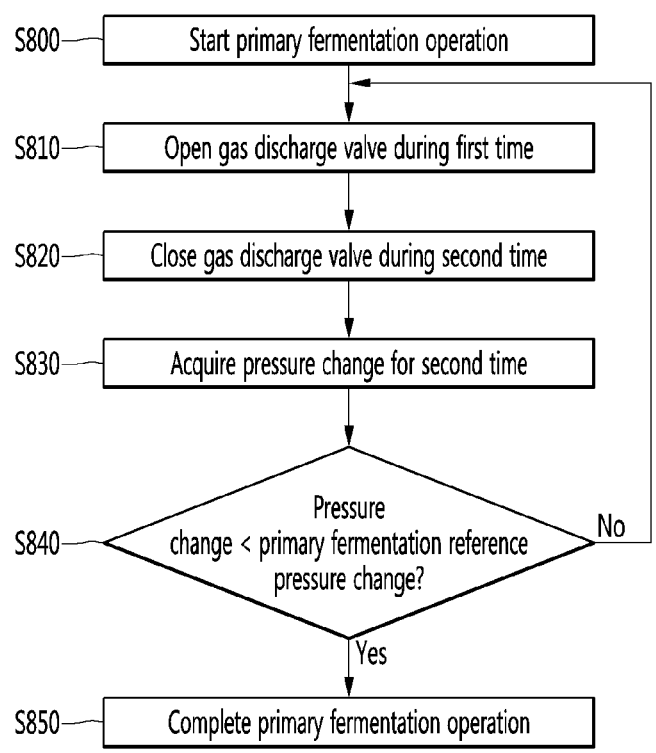
FIG. 8 is a flowchart of an operation in which a fermentation and aging apparatus according to an embodiment detects completion of a primary fermentation operation based on change in pressure measured through a gas pressure sensor.

Hereinafter, embodiments related to primary and secondary fermentation operations performed by the fermentation and aging apparatus will be described with reference to FIGS. 8 and 9. FIG. 8 is a flowchart of an operation in which a fermentation and aging apparatus according to an embodiment detects completion of a primary fermentation operation based on pressure change measured through a gas pressure sensor.

Referring to FIG. 8, as the fermentation and aging apparatus starts the primary fermentation operation (S800), the gas discharge valve 73 may be opened for a preset or predetermined first time (S810). As the primary fermentation operation starts, the fermentation accelerator, for example, yeast, introduced into the fermentation container 12 may perform fermentation with respect to the object to be fermented, for example, malt. During initial fermentation, off-flavor may occur according to fermentation. When off-flavor remains in the beverage which is being made, the flavor of the made beverage may deteriorate.

The controller 460 may open the gas discharge valve 73 for the first time during the primary fermentation operation, thereby discharging gas including off-flavor. In addition, as the gas discharge channel 71 is opened, it is possible to prevent the internal pressure of the fermentation container 12 from excessively increasing. By discharging off-flavor and preventing the internal pressure from increasing, it is possible to minimize an increase in stress of the fermentation accelerator, thereby leading to smooth fermentation of the fermentation accelerator in the primary fermentation operation.

The first time may be set differently according to a type of the beverage, without being limited thereto. When the first time has elapsed, the fermentation and aging apparatus may close the gas discharge valve 73 for a preset or predetermined second time (S820), and acquire pressure change for the second time using the gas pressure sensor 72 (S830). The controller 460 may close the gas discharge valve 73 after the first time has elapsed, thereby closing the gas discharge channel 71.

The controller 460 may measure the internal pressure of the fermentation container 12 using the gas pressure sensor 72 while closing the gas discharge channel 71 for the preset or predetermined second time. For example, the controller 460 may measure a first pressure when the gas discharge valve 73 is closed and measure a second pressure when the second time has elapsed, using the gas pressure sensor 72. The controller 460 may acquire a pressure change during the second time based on a difference between the measured first pressure and the second pressure. The second time may be set differently according to a type of the made beverage, without being limited thereto.

When the acquired pressure change is equal to a predetermined primary fermentation reference pressure change (NO of S840), the fermentation and aging apparatus may detect that the primary fermentation operation is incomplete and may perform operations S810 to S830 again. When the acquired pressure change is greater than the primary fermentation reference pressure change, this may mean that primary fermentation is not sufficiently performed. In this case, gas including off-flavor according to fermentation of the fermentation accelerator may be still generated. Accordingly, the controller 460 may open the gas discharge valve 73 to open the gas discharge channel 71 again for the first time. The primary fermentation reference pressure change may vary according to the type of the made beverage, without being limited thereto.

In contrast, when the acquired pressure change is lower than the predetermined primary fermentation reference pressure change (YES of S840), the fermentation and aging apparatus may complete the primary fermentation operation (S850). As the progress time of the primary fermentation elapses, the degree of fermentation increases, thereby gradually decreasing the amount of gas including off-flavor. Therefore, the pressure change during the second time may also decrease. The controller 460 may detect that the primary fermentation operation is complete when the acquired pressure change is lower than the primary fermentation reference pressure change.

Figure 9:
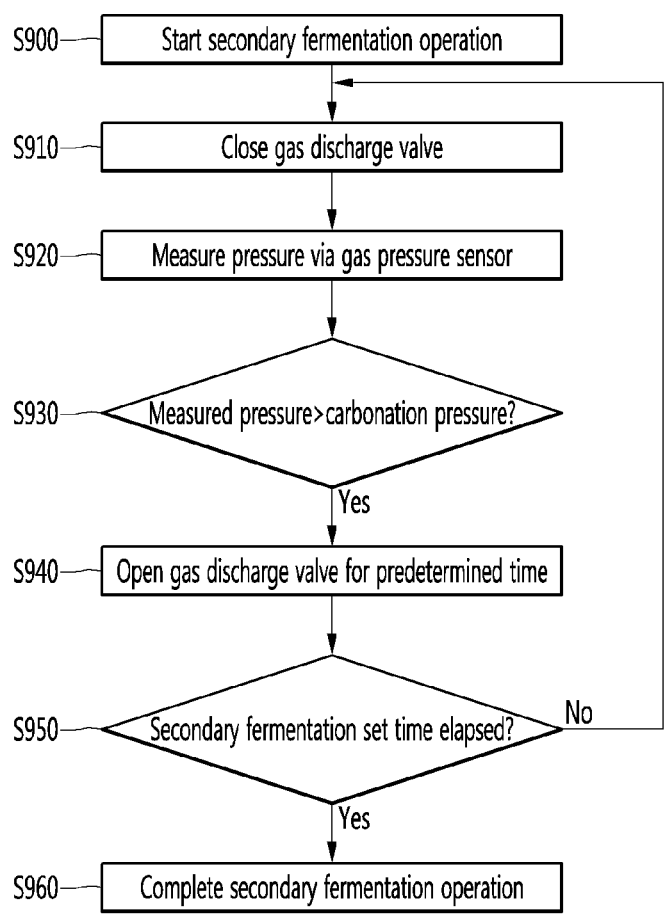
FIG. 9 is a flowchart illustrating a control operation of the fermentation and aging apparatus during a secondary fermentation operation.

FIG. 9 is a flowchart of a control operation of the fermentation and aging apparatus during a secondary fermentation operation. Referring to FIG. 9, the fermentation and aging apparatus may start a secondary fermentation operation (S900), when detecting that the primary fermentation operation is complete as described above with respect to FIG. 8. As the secondary fermentation operation starts, the fermentation and aging apparatus may close the gas discharge valve 73 (S910).

The fermentation and aging apparatus may periodically measure pressure using the gas pressure sensor 72 (S920). The secondary fermentation operation is to produce carbonic acid in the beverage, and carbon dioxide gas may be generated in the fermentation container 12. As the gas discharge valve 73 is closed, the internal pressure of the fermentation container 12 may gradually increase as the carbon dioxide gas is generated. When the internal pressure of the fermentation container 12 increases to a predetermined pressure or more, some of the carbon dioxide gas may be dissolved and carbonated in the beverage.

When the measured pressure is higher than preset or predetermined carbonation pressure (YES of S930), the fermentation and aging apparatus may open the gas discharge valve 73 for a predetermined period of time (S940). The preset or predetermined carbonation pressure may correspond to a state in which a predetermined amount of carbonic acid is dissolved in the beverage, and may be set differently according to a type of the made beverage. As the set value of the carbonation pressure increases, the amount of carbonic acid dissolved in the made beverage may increase.

The controller 460 may open the gas discharge valve 73 to discharge some of the carbon dioxide gas, when the pressure measured through the gas pressure sensor 72 is higher than the carbonation pressure.

The fermentation and aging apparatus may determine whether a progress time of the secondary fermentation operation exceeds a preset or predetermined secondary fermentation time (S950). The secondary fermentation time may be set differently according to a type of the made beverage.

When the progress time of the secondary fermentation operation does not exceed the secondary fermentation time (NO of S950), the fermentation and aging apparatus may repeatedly perform operations S910 to S940. As operations S910 to S940 are repeatedly performed, appropriate stress pressure may be applied to the fermentation accelerator according to change in internal pressure of the fermentation container 12. Therefore, natural carbonation through the fermentation accelerator may be effectively performed.

When the progress time of the secondary fermentation operation exceeds the secondary fermentation time (YES of S950), the fermentation and aging apparatus may detect completion of the secondary fermentation operation (S960). That is, according to the embodiment shown in FIG. 9, the fermentation and aging apparatus may control the pressure of the fermentation container 12 during the secondary fermentation operation, thereby enabling effective natural carbonation of the beverage by the fermentation accelerator.

According to embodiments is disclosed herein, the fermentation and aging apparatus may accurately control the temperature of the hot fluid supplied to the fermentation container to the target temperature in the hot fluid supply operation. That is, as the temperature of the hot fluid introduced into the fermentation container may be maintained at the target temperature regardless of the temperature of the fluid accommodated in the tank or the external temperature, it is possible to uniformly maintain a quality of the made beverage.

In addition, the fermentation and aging apparatus may control the degree of opening of the flow rate control valve according to change in temperature of the fluid introduced into the fermentation tank, thereby preventing the degree of opening of the flow rate control valve from being excessively frequently controlled. Therefore, more efficient control is possible and risk of damage to the flow rate control valve may be reduced.

In addition, the fermentation and aging apparatus may effectively control the fermentation operation based on the internal pressure of the fermentation container. In addition, the fermentation and aging apparatus may control the internal pressure of the fermentation container, thereby enabling effective natural carbonation of the beverage by the fermentation accelerator.

Embodiments disclosed herein provide a fermentation and aging apparatus capable of automatically controlling the temperature of hot fluid introduced into a fermentation tank or a fermentation container according to a target temperature. Embodiments disclosed herein further provide a fermentation and aging apparatus capable of effectively controlling primary fermentation and secondary fermentation according to pressure acquired using a gas pressure sensor.

The fermentation and aging apparatus according to embodiments disclosed herein may perform a hot fluid supply operation of heating fluid accommodated in a tank and supplying the fluid to a fermentation container while beverage is made. During the hot fluid supply, the controller of the fermentation and aging apparatus may measure the temperature of fluid passing through the heater and control the degree of opening of the flow rate control valve based on the measured temperature, thereby controlling the temperature of fluid introduced into the fermentation container to a target temperature.

According to embodiments disclosed herein, the controller may increase the degree of opening of the flow rate control valve when the measured temperature is higher than a preset or predetermined target temperature, thereby increasing the flow rate of the fluid passing through the heater. In contrast, when the measured temperature is lower than the target temperature, the controller may decrease the degree of opening of the flow rate control valve, thereby decreasing the flow rate of the fluid passing through the heater.

According to embodiments disclosed herein, the controller may more intelligently control the flow rate control valve according to temperature change through the measured temperature and a previously measured temperature. For example, the controller may maintain the degree of opening of the flow rate control valve when the measured temperature is lower than the target temperature and the measured temperature is higher than the previously measured temperature. In contrast, the controller may decrease the degree of opening of the flow rate control valve when the measured temperature is lower than the target temperature and the measured temperature is equal to or less than the previously measured temperature.

In another example, the controller may maintain the degree of opening of the flow rate control valve when the measured temperature is higher than the target temperature and the measured temperature is lower than the previously measured temperature. In contrast, the controller may increase the degree of opening of the flow rate control valve when the measured temperature is higher than the target temperature and the measured temperature is equal to or greater than the previously measured temperature. Therefore, it is possible to prevent the degree of opening of the flow rate control valve from being excessively frequently controlled.

The controller may measure the flow rate of fluid discharged from the tank using a flow meter, calculate the amount of supplied fluid based on the measured flow rate, and turn off the pump and the heater when the calculated amount of supplied fluid reaches a set or predetermined amount. The controller may perform a first fermentation operation and a second fermentation operation while the beverage is made. The controller may accurately detect whether the primary fermentation operation is complete based on an internal pressure change of the fermentation container measured through the gas pressure sensor during the primary fermentation operation. The controller may control the internal pressure of the fermentation container such that a predetermined amount of carbonic acid is dissolved in the beverage.

The foregoing description is merely illustrative of the technical idea, and various changes and modifications may be made by those skilled in the art without departing from the essential characteristics of the present disclosure. Therefore, embodiments disclosed herein are to be construed as illustrative and not restrictive, and the scope of the technical idea is not limited by these embodiments. The scope should be construed according to the following claims, and all technical ideas within equivalency range of the appended claims should be construed as being included in the scope.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A fermentation and aging apparatus, comprising:
a tank in which a fluid is accommodated;
a fermentation container forming a space in which the fluid discharged from the tank is accommodated;
a pump disposed in a channel between the tank and the fermentation container to supply the fluid accommodated in the tank to the fermentation container;
a flow rate control valve configured to control a flow rate of the fluid discharged from the tank;
a heater configured to heat fluid discharged from the tank;
a temperature sensor configured to measure a temperature of the fluid passing through the heater; and
a controller configured to control a degree of opening of the flow rate control valve based on the measured temperature, wherein the controller is configured to:
periodically measure the temperature of the fluid passing through the heater through the temperature sensor; and
control the degree of opening of the flow rate control valve based on the measured temperature, a predetermined target temperature, and a previously measured temperature, wherein the controller maintains the degree of opening of the flow rate control valve when the measured temperature is lower than the predetermined target temperature and the measured temperature is higher than the previously measured temperature, and decreases the degree of opening of the flow rate control valve when the measured temperature is lower than the predetermined target temperature and the measured temperature is equal to or less than the previously measured temperature.

2. The fermentation and aging apparatus of claim 1, wherein the controller increases the degree of opening of the flow rate control valve when the measured temperature is higher than a predetermined target temperature, and decreases the degree of opening of the flow rate control valve when the measured temperature is lower than the predetermined target temperature.

3. The fermentation and aging apparatus of claim 1, wherein the flow rate control valve includes a step motor, and wherein the controller controls a degree of opening of the flow rate control valve, by controlling a step of the step motor.

4. The fermentation and aging apparatus of claim 3, wherein the controller increases the step of the step motor by a predetermined step when the measured temperature is higher than the predetermined target temperature, and decreases the step of the step motor by a predetermined step when the measured temperature is lower than the predetermined target temperature.

5. The fermentation and aging apparatus of claim 1, wherein the temperature sensor is installed in the heater or between the heater and the fermentation container.

6. The fermentation and aging apparatus of claim 1, further comprising a flow meter configured to measure a flow rate of the fluid discharged from the tank, wherein the controller is configured to calculate an amount of fluid based on the flow rate measured by the flow meter and turn off the pump and the heater when the calculated amount of supplied fluid reaches a predetermined amount.

7. A fermentation and aging apparatus, comprising:
a tank in which a fluid is accommodated;
a fermentation container forming a space in which the fluid discharged from the tank is accommodated;
a pump disposed in a channel between the tank and the fermentation container to supply the fluid accommodated in the tank to the fermentation container;
a flow rate control valve configured to control a flow rate of the fluid discharged from the tank;
a heater configured to heat fluid discharged from the tank;
a temperature sensor configured to measure a temperature of the fluid passing through the heater; and
a controller configured to control a degree of opening of the flow rate control valve based on the measured temperature, wherein the controller is configured to:

periodically measure the temperature of the fluid passing through the heater through the temperature sensor; and control the degree of opening of the flow rate control valve based on the measured temperature, a predetermined target temperature, and a previously measured temperature, wherein the controller maintains the degree of opening of the flow rate control valve when the measured temperature is higher than the predetermined target temperature and the measured temperature is lower than the previously measured temperature, and increases the degree of opening of the flow rate control valve when the measured temperature is higher than the target temperature and the measured temperature is equal to or greater than the previously measured temperature.

8. The fermentation and aging apparatus of claim 7, wherein the flow rate control valve includes a step motor, and wherein the controller controls a degree of opening of the flow rate control valve, by controlling a step of the step motor.

9. The fermentation and aging apparatus of claim 8, wherein the controller increases the step of the step motor by a predetermined step when the measured temperature is higher than the predetermined target temperature, and decreases the step of the step motor by a predetermined step when the measured temperature is lower than the predetermined target temperature.

10. The fermentation and aging apparatus of claim 7, wherein the temperature sensor is installed in the heater or between the heater and the fermentation container.

11. The fermentation and aging apparatus of claim 7, further comprising a flow meter configured to measure a flow rate of the fluid discharged from the tank, wherein the controller is configured to calculate an amount of fluid based on the flow rate measured by the flow meter and turn off the pump and the heater when the calculated amount of supplied fluid reaches a predetermined amount.

* * * * *